US012731420B2

(12) United States Patent
Debski et al.

(10) Patent No.: US 12,731,420 B2
(45) Date of Patent: Sep. 8, 2026

(54) METHOD AND SYSTEM FOR PREDICTION OF MICROORGANISM GROWTH USING ARTIFICIAL INTELLIGENCE

(71) Applicant: Bacteromic Sp. z o.o., Warsaw (PL)

(72) Inventors: Pawel Debski, Warsaw (PL); Krystian Kurek, Magnuszew (PL); Michal Bortkiewicz, Gdansk (PL); Justyna Szeluga, Bialystok (PL)

(73) Assignee: BACTEROMIC SP. Z.O.O., Warsaw (PL)

( * ) Notice: Subject to any disclaimer, the term of this patent is extended or adjusted under 35 U.S.C. 154(b) by 264 days.

(21) Appl. No.: 18/291,176

(22) PCT Filed: Jul. 29, 2022

(86) PCT No.: PCT/EP2022/071396

§ 371 (c)(1),
(2) Date: Jan. 22, 2024

(87) PCT Pub. No.: WO2023/006967

PCT Pub. Date: Feb. 2, 2023

(65) Prior Publication Data

US 2024/0282126 A1 Aug. 22, 2024

(30) Foreign Application Priority Data

Jul. 30, 2021 (EP) .................................... 21188827

(51) Int. Cl.
*G06V 20/69* (2022.01)
*C12Q 1/18* (2006.01)
(Continued)

(52) U.S. Cl.
CPC ............. *G06V 20/698* (2022.01); *C12Q 1/18* (2013.01); *G06T 5/50* (2013.01); *G06V 10/82* (2022.01); *G06T 2207/10061* (2013.01)

(58) Field of Classification Search
CPC ........ G06V 20/698; G06V 10/82; G06T 5/50; G06T 2207/10056; G06T 2207/10061; C12Q 1/18; G06N 3/0464
See application file for complete search history.

(56) References Cited

U.S. PATENT DOCUMENTS

2018/0336880 A1* 11/2018 Arik ........................ G10L 25/30
2019/0294929 A1* 9/2019 Yao ........................ G06N 3/082
(Continued)

FOREIGN PATENT DOCUMENTS

EP 3597768 1/2020 ............... C12Q 1/18
WO WO2019185885 10/2019 .............. C12M 3/06
(Continued)

OTHER PUBLICATIONS

Alexander Gomez Villa, Augusto Salazar, and Igor Stefanini. "Counting Cells in Time-Lapse Microscopy using Deep Neural Networks". In: arXiv:1801.10443 [cs] (Jan. 2018). arXiv: 1801.10443.
(Continued)

*Primary Examiner* — Shaghayegh Azima
(74) *Attorney, Agent, or Firm* — HAYES SOLOWAY P.C.

(57) ABSTRACT

Disclosed is a computer-implemented method for real-time prediction of microorganism growth or microorganism growth inhibition of a microorganism inoculum in a phenotypic antimicrobial susceptibility test (AST) as well as a rapid antimicrobial susceptibility testing system respectively using artificial intelligence.

19 Claims, 11 Drawing Sheets

(51) Int. Cl.

| | |
|---|---|
| ***G06T 5/50*** | (2006.01) |
| ***G06V 10/82*** | (2022.01) |

(56) References Cited

U.S. PATENT DOCUMENTS

| | | | | |
|---|---|---|---|---|
| 2021/0130868 | A1 * | 5/2021 | Tao | G16H 50/20 |
| 2022/0164934 | A1 * | 5/2022 | Gao | G06N 3/09 |
| 2022/0201316 | A1 * | 6/2022 | Coelho | G06N 3/0464 |
| 2022/0230519 | A1 * | 7/2022 | Wellhausen | G06N 3/0495 |
| 2023/0007284 | A1 * | 1/2023 | Li | H04N 19/159 |
| 2023/0206063 | A1 * | 6/2023 | Condurache | G06N 3/08<br>706/25 |

FOREIGN PATENT DOCUMENTS

| | | | |
|---|---|---|---|
| WO | WO2019185927 | 10/2019 | C12M 1/32 |
| WO | WO2021067170 | 4/2021 | C12Q 1/18 |
| WO | WO-2021067170 A1 * | 4/2021 | H04N 23/56 |

OTHER PUBLICATIONS

International Search Report (with English translation) and Written Opinion issued in PCT/EP2022/071396, dated Nov. 24, 2022, 8 pages.

International Preliminary Report on Patentability (with English translation) issued in PCT/EP2022/071396, dated May 24, 2023, 7 pages.

Villa et al., Counting Cells in Time-Lapse Microscopy using Deep Neural Networks, Scuola universitaria professionale della Svizzera italiana (SUPSI), Grupo de investigacion Sistemic, Jan. 31, 2018, 8 pages.

Xingjian Shi et al. “Convolutional LSTM Network: A Machine Learning Approach for Precipitation Nowcasting”. In: arXiv:1506. 04214 [cs] (Sep. 2015). arXiv: 1506.04214 version: 2.

Wang et al.: “Early detection and classification of live bacteria using timelapse coherent imaging and deep learning”. In: Light: Science & Applications 9.1 (Jul. 2020). No. 1 Publisher: Nature Publishing Group, p. 118. ISSN: 2047-7538. DOI: 10.1038/s41377-020-00358-9.

Zhaofan Qiu, Ting Yao, and Tao Mei. “Learning Spatio-Temporal Representation with Pseudo-3D Residual Networks”. In: arXiv:1711. 10305 [cs] (Nov. 2017). arXiv: 1711.10305.

* cited by examiner

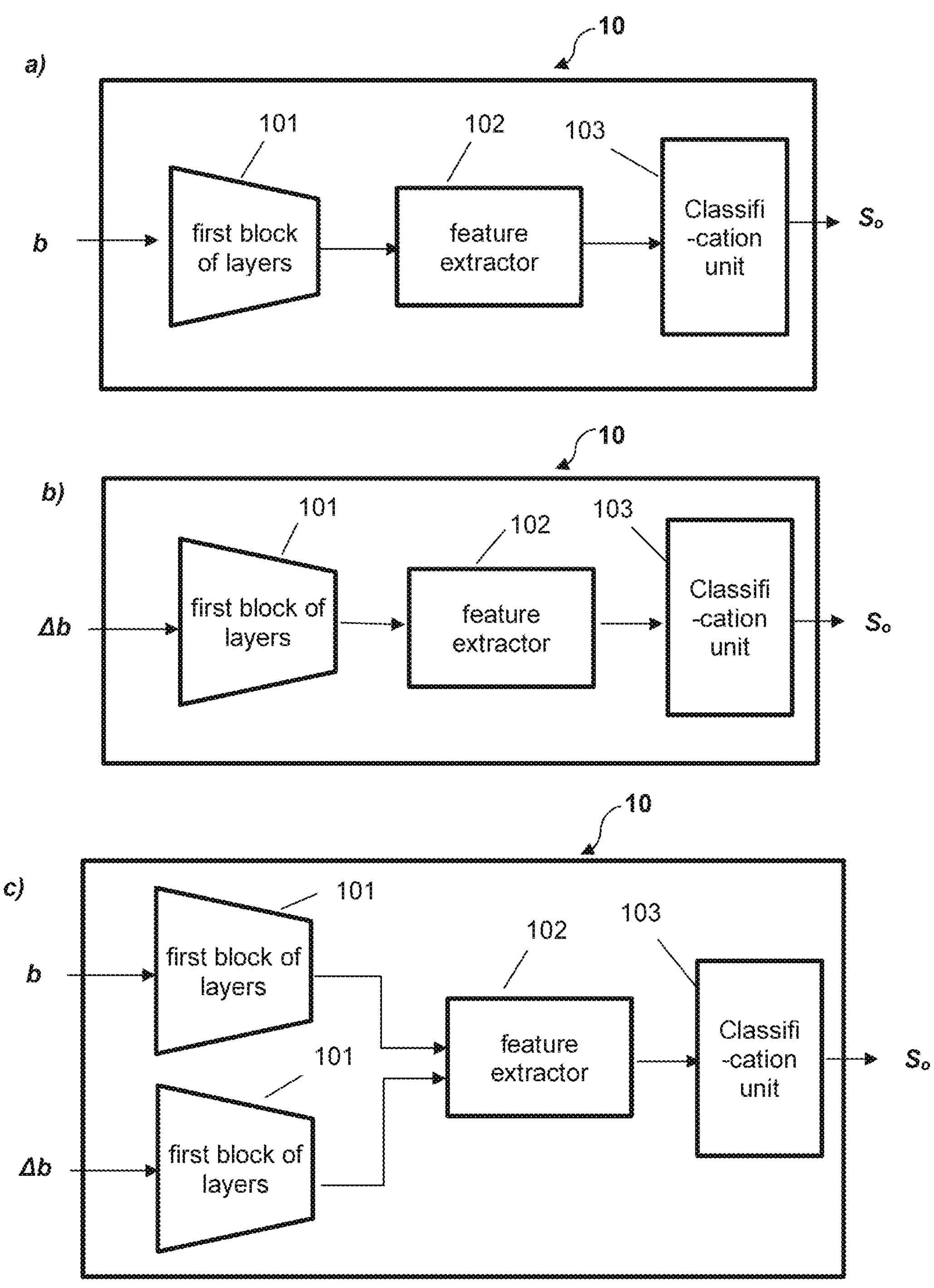
Figs. 2 a), b), c)

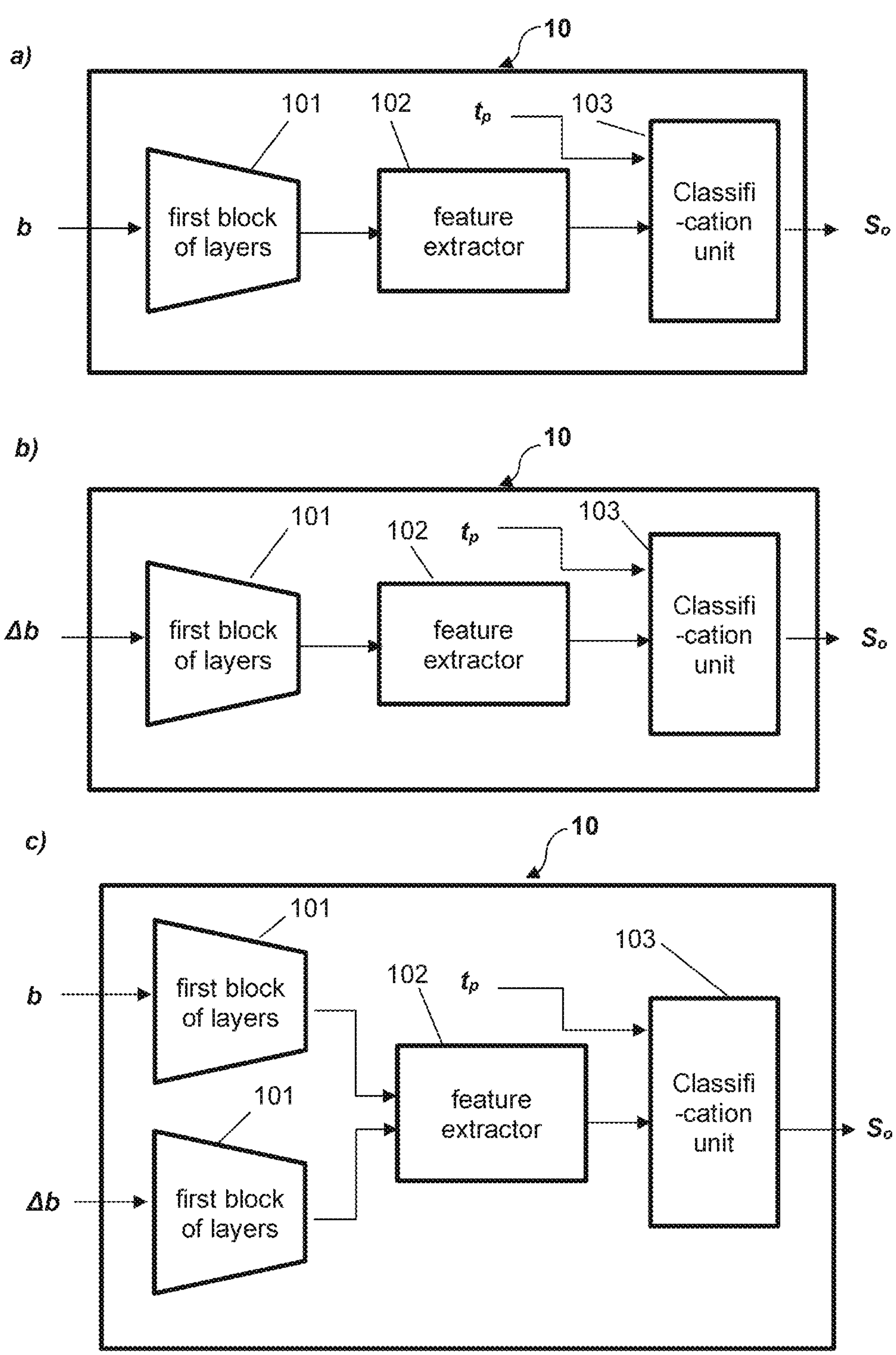
Figs. 3 a), b), c)

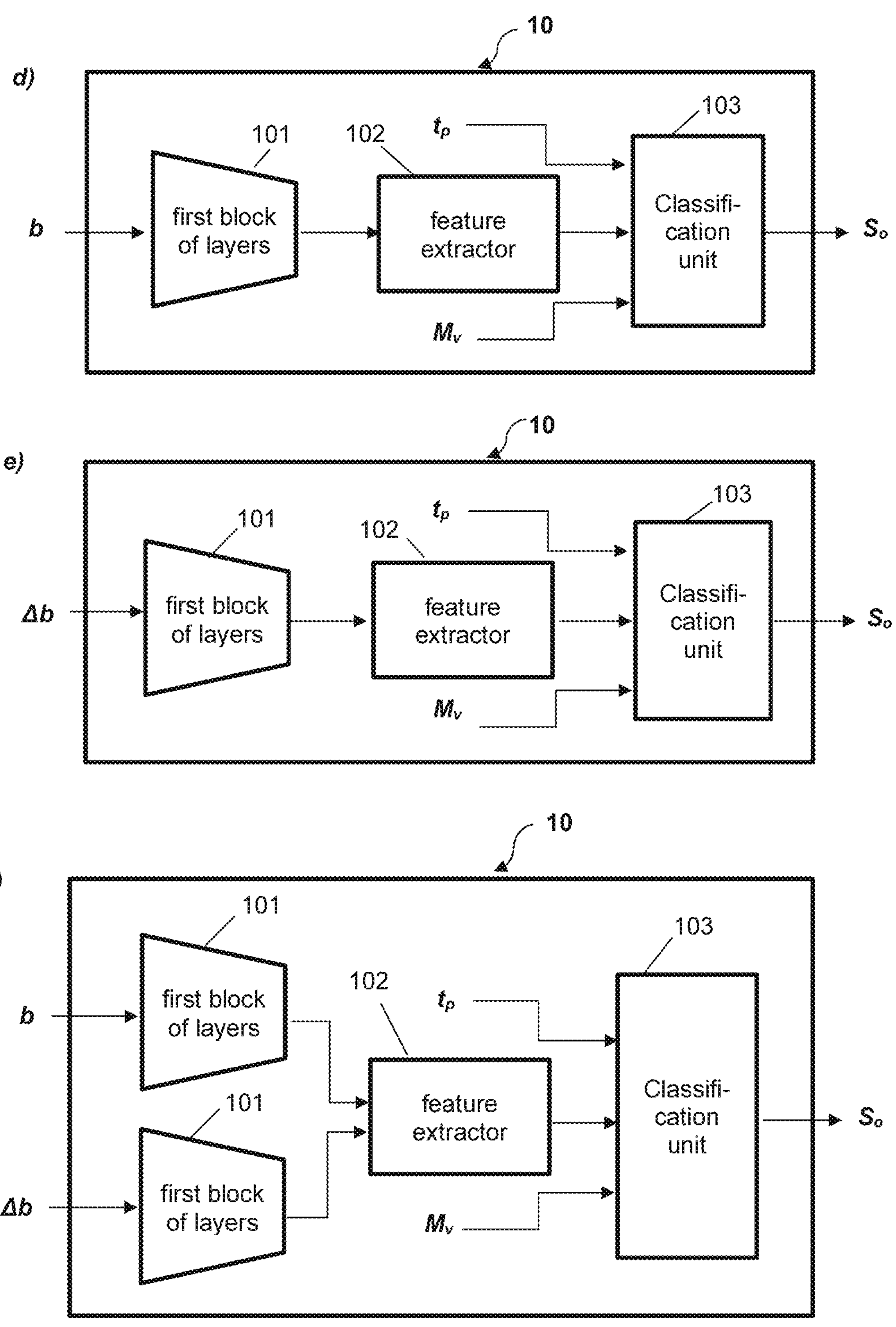
Figs. 3 d), e), f)

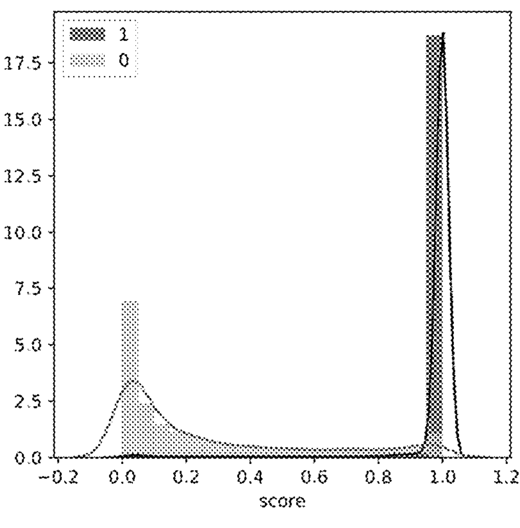
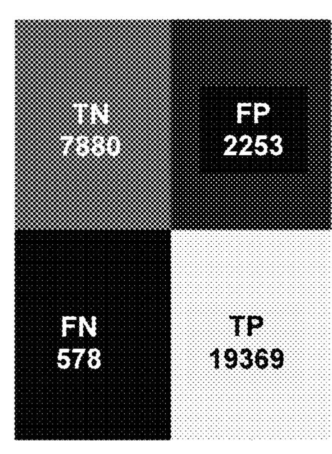
Fig. 8a)
Fig. 8b)
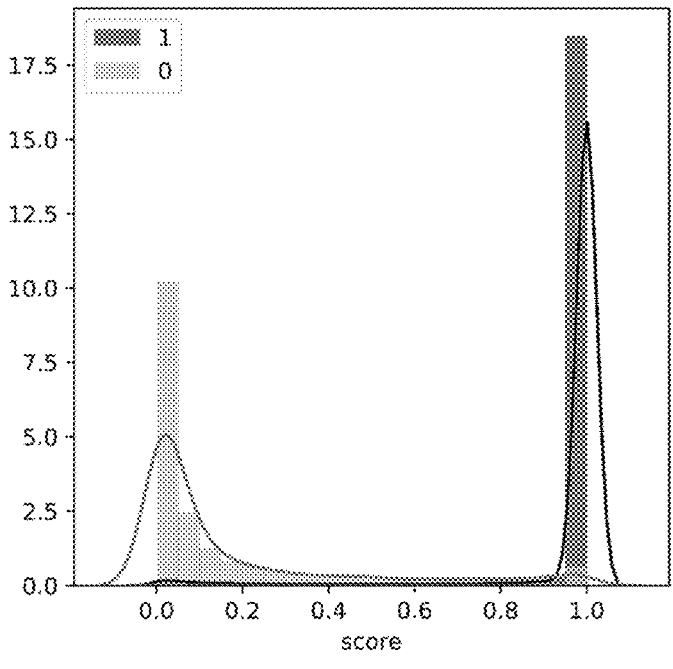
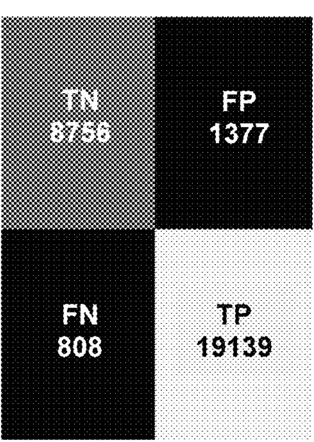
Fig. 9a)
Fig. 9b)

METHOD AND SYSTEM FOR PREDICTION OF MICROORGANISM GROWTH USING ARTIFICIAL INTELLIGENCE

FIELD OF INVENTION

The present invention relates to a computer-implemented method for real-time prediction of microorganism growth or microorganism growth inhibition of a microorganism inoculum in a phenotypic antimicrobial susceptibility test (AST) as well as a rapid antimicrobial susceptibility testing system respectively using artificial intelligence.

BACKGROUND

In clinical microbiology, infections caused by microorganisms selected from the group consisting of bacterium, *mycobacterium* and fungus may only be effectively treated when the respective microorganism is susceptible to a respective antimicrobial agent. This is in particular important in view of multidrug resistant microbial pathogens, which require a precise information on Antimicrobial Susceptibility Testing (AST). In this case one or more isolates (samples) of the microorganisms are respectively incubated in the presence of one or a combination of two or more antimicrobials and it is assessed whether growth of the respective isolate population occurs.

The Antimicrobial Susceptibility Testing allows for qualitative determination whether the isolate of the microorganism is SUSCEPTIBLE (S), INTERMEDIATE (I) or RESISTANT (R) in view of the antimicrobials used.

Thereby the category SUSCEPTIBLE indicates that the antimicrobial/combination of antimicrobials may be an appropriate choice for treating the infection caused by the microorganism tested and bacterial/fungal resistance is absent or at a clinically insignificant level.

The category INTERMEDIATE indicates that the tested isolate populations of the microorganism are “moderately susceptible” to the tested antimicrobial, whereby this category serves as a buffer zone between SUSCEPTIBLE and RESISTANT. Antimicrobials falling in this category may still be indicated in case they can be concentrated at the focus of infection (e.g., quinolones and β-lactam in urine) or when a higher than normal dosage of the antimicrobial can be used (e.g., β-lactam) because of its low toxicity. The antimicrobial agent may still be effective against the tested isolate but response rates may be lower than for susceptible isolates.

The category RESISTANT indicates that the tested isolate is resistant to the respective antimicrobial, which means that the growth of bacterial or fungal microorganism does not seem to be inhibited by the usually achievable concentrations of the tested antimicrobial agent with normal dosage schedules. Thus, antimicrobials of this category may not be regarded as appropriate choice for treating the infection caused by the tested resistant bacterial or fungal isolate/sample.

Alternatively, the Wild type (WT) or Non Wild type (NWT) may be used to categorize the susceptibility of the microorganism. Accordingly, a microorganism isolate may be defined as WT for a species by the absence of phenotypically detectable acquired and mutational resistance mechanisms to the antimicrobial agent in question. This means in turn, that a microorganism isolate may be defined as NWT for a species by the presence of phenotypically detectable acquired or mutational resistance mechanisms to the antimicrobial agent in question.

In addition, the Antimicrobial Susceptibility Testing method allows for a quantitative evaluation by determining the minimum inhibitory concentration (MIC) of an antimicrobial for the particular isolate, whereby an antimicrobial dilution assay may be conducted in agar, within culture tubes or within microtiter plates. When determining the MIC within culture tubes or microtiter plates, serial dilutions of a single antimicrobial or a combination of two or more antimicrobials may be inoculated into the well or tube alongside a standard inoculum of a sample microorganism. Microbial growth in the presence of the respective antimicrobial concentration is generally measured using turbidity. Minimum inhibitory concentration refers to the highest dilution or lowest concentration of antimicrobial that completely inhibits growth of the isolate. When using the MIC method on agar, e.g., an inoculated diffusion strip containing an antimicrobial concentration gradient is applied to the agar so that the gradient transfers from the strip into the agar. After overnight incubation or longer, an elliptical zone of inhibition centered around the strip is formed. The MIC value can be read at the point the ellipse edge intersects the MIC strip. The resulting MIC value can then be interpreted using standards such as provided by European Committee on Antimicrobial Susceptibility testing (EUCAST) or Clinical & Laboratory Standards Institute (CLSI).

Although phenotypic assays of antimicrobial resistance are very reliable, many of them are also very time consuming, as the proliferation rate of the microorganisms in particular slows down after inoculating the isolated sample microorganism into new culture medium. Such a slow-down may be observed as so-called lag phase of bacterial growth in batch culture. Although for fast-growing bacteria tests there exists according to the FDA the possibility of a “short-term incubation” with less than 16 hours, the standard incubation time generally rages between 16 to 20 hours. Accordingly, the attending physician may obtain the results of the Antimicrobial Susceptibility Testing at least within days or weeks.

In view of the threats posed by, possibly lethal, infections caused by antimicrobial resistant microorganisms and the increase of worldwide spread of microorganisms and, thus, also of resistance to antimicrobial agents, rapid access to the AST information including of such resistant species, and determination of minimum inhibitory concentrations is, however, increasingly desired. Such an expedited access of the AST information may increase the precision of antimicrobial therapy, may thus reduce the risk of complications in the treatment of microbial infections and at the same time may reduce the hospitalization time and costs of antimicrobial treatment.

In order to expedite the access to AST information and/or in order to increase precision of the AST information, automated computer-implemented methods and systems for rapidly testing antimicrobial susceptibility are provided, e.g., in EP 3 597 768 B1 (in the name of Bacteromic Sp. z o.o.). This patent provides expedited access to the AST information, as the qualitative and quantitative susceptibility of an inoculated microorganism against an antimicrobial agent or a combination of antimicrobial agents is determined in the lag phase as a function of one or more slopes of linear trends $\alpha$ of readout values. This method, however, requires the measurement of chemical or physical properties of the inoculated microorganism using suitable detection systems during incubation and, thus, the detection means may be dependent on the specific microorganism to be detected.

Machine learning models based on artificial neural networks, in particular convolutional networks, are at the forefront of problems related to the classification of photos and videos. Their advantage results mainly from the interpretation of whole, unprocessed photos excluding normalization or standardization.

Convolutional Neural Networks (CNN) benefit in terms of efficiency from the concept of shared parameter, in other terms each filter in every layer is applied on every possible region of the output of the previous layer. Networks model convert signal (image/video/audio etc.) into a set of features, which for instance are used to classify the signal by a forward pass through the sequence of layers. Most layers of the model may be regarded as feature extractor layers. The binary classification task or other tasks of the CNN are generally performed by the last layer of the model. The set of features is rarely explainable and differs between models due to their architecture and training process, but they can be interpreted as condensed information about the content of a photo or video.

Recurrent/Recursive Neural Networks (RNN), such as Long Short-Term Memory (LSTM) cells, are generally able to store and retrieve information about changes in the analyzed process over temporal dimensions of the input. Thus, RNN support the operation of convolutional networks in problems related to the classification of videos, as they are able to store and reuse information about changes in the analyzed process over time. In other words, RNN are networks in which information about what happened before and what happened later is transferred between neurons in a manner that represents time dimension using convenient sequential processing representation that is absent in most of other neural network architectures.

Villa et al. provide in their work (see Alexander Gomez Villa, Augusto Salazar, and Igor Stefanini. "Counting Cells in Time-Lapse Microscopy using Deep Neural Networks". In: arXiv:1801.10443 [cs] (January 2018). arXiv: 1801.10443) a method for counting cells using time-lapse microscopy by incorporating an approach of dynamic cell counting based on LSTM recurrent neural networks. In their approach, the first step uses a convolutional neural networks that independently processes consecutive images (their regions of particular shape—crops) to extract spatial features. In the second step, those features are subsequently fed to a recurrent neural network with LSTM cells to eventually be processed by Join algorithm that takes into account overlapping crops and returns number of cells. The technique proposed by Villa et al., however, only allows to count bacteria, but not to detect microorganism growth or microorganism growth inhibition. Furthermore, high spatial resolution imaging microscopic devices, i.e. a spatial resolution of <0.01 mm/pixel are necessary in order to provide the necessary input data.

Wang et al. present in their work (see Hongda Wang et al. "Early detection and classification of live bacteria using time-lapse coherent imaging and deep learning". en. In: Light: Science & Applications 9.1 (July 2020). Number: 1 Publisher: Nature Publishing Group, p. 118. ISSN: 2047-7538. DOI: 10.1038/s41377-020-00358-9) a bacteria detection system with subsequent bacteria classification on images captured with a holographic microscope. The neural models were based on Pseudo-3D Residual Networks (see Zhaofan Qiu, Ting Yao, and Tao Mei. "Learning Spatio-Temporal Representation with Pseudo-3D Residual Networks". In: arXiv:1711.10305 [cs] (November 2017). arXiv: 1711.10305). The architecture of the proposed image processing model uses four elements that may be divided into two steps, namely detection step and classification step. The first step comprises an initial processing module based on classic image processing techniques and differential analysis. This initial processing module is responsible for selecting regions of interest on the agar plate for further analysis. A second processing module is following in the first step using a neural detection network (DN) that eliminates the presence of nonbacterial objects from the list of selected regions of interest to keep only the growing microorganism colonies (true positives). For the detection network Wang et al. uses running windows of size 4×0:5=2 h of complex valued images (i.e., phase and amplitude values obtained by a microscope) as an input to this model. The second step further classifies the species of the detected colonies using a neural classification network model (CN) following a similar network architecture to DN. The CN takes as an input running windows of size 8×0:5=4 h of the complex valued images. Because the detection network and the classification network differ in the number of images and, thus, in the analysis time, the method of Wang et al. exhibits a time lag of at least 2 hours between bacteria detection and bacteria classification. Thus, this method does not provide an online prediction of bacterial growth. Furthermore, the method of Wang et al. is again limited in view of the provision of the high spatial resolution images comprising phase and amplitude values obtained by the respective high resolution microscope having a spatial resolution of <0.01 mm/pixel.

WO 2021/067170 A1 refers to embodiments that allow for rapid antimicrobial susceptibility testing (AST) that may use changes in the pixel intensity in reflected light from wells comprising differently double-diluted antimicrobials to determine microorganism growth and antimicrobial resistance. In this regard doubling dilutions of an antimicrobial have to be added to a standard well plate or other tray. In addition, pathogen or other microorganism must be added to the dilutions in the well plate. The well plate must be incubated for a respective time period, such as less than 3 hours. Only after incubation, the well plate must be imaged and the resulting image data is analyzed. WO 2021/067170 A1 further teaches that wells where the microorganism is able to grow appear darker or lighter than wells where the microorganism does not grow. Differences in pixel intensity of the differently diluted wells are used to determine the susceptibility or resistance of the microorganism in the respective doubling-dilutions to the antimicrobial. Even in case the plate would be scanned at more than one time point, the pixel intensities of only one image is used to predict the microorganism growth or no growth, which is shown in graphs 510, 520, 530 and 540, which respectively use only the image taken after 1.5, 2, 3 or 4 hours of incubation respectively. Thus, WO 2021/067170 A1 uses as input data the pixel intensity of the image taken at one time point versus the doubling-dilution concentration of the differently diluted antimicrobials in the respective well for carrying out the estimation of the MIC including a positive control reference. The use of the pixel intensity of an image taken at one specific time point renders the method sensitive to processing anormalities, such as air bubbles etc., which influence the pixel intensity in reflected light.

In view of the prior art, there still exists a need in providing a method and system for real-time prediction of microorganism growth or microorganism growth inhibition of a microorganism inoculum in a phenotypic antimicrobial susceptibility test (AST), which enables a real-time prediction of microorganism growth or no-growth without the need of providing highly resolved images having a spatial resolution of <0.01 mm/pixel as input data. In particular, when using high throughput tests having a large array of incubation chambers, e.g. >1,000 incubation chambers, preferably 1,500 or 3,000 incubation chambers. Preferably, the method may provide a possibility for tuning the trade-off between sensitivity and specificity. Moreover, the method preferably may be less sensitive and, thus, more robust, in view of processing anomalies, such as air bubbles. In addition, the method preferably may provide suitable performance metrics even for input data provided by a different system than used for providing the training data.

SUMMARY OF INVENTION

One or more of the above mentioned needs is/are solved by the subjects of the independent claims of the present invention. Advantages (preferred embodiments) are set out in the detailed description hereinafter and/or the accompanying figures as well as in the dependent claims.

Accordingly, a first aspect of the present invention relates to a computer-implemented method for real-time prediction of microorganism growth or microorganism growth inhibition of a microorganism inoculum in a phenotypic antimicrobial susceptibility test (AST), characterized in that the method comprises or consists of the following steps:

a) Incubating a sample of a microorganism with a suitable incubating device, wherein the incubated sample comprises a single antimicrobial agent or a combination of antimicrobial agents, b) Taking a sequence of two or more digital images of the incubated sample microorganism of step a) with a suitable imaging device and providing information on pixel intensity ($p_i$) per pixel of the respective images, wherein the sequence of images is consecutively distributed within a progress value ($t_p$) with $0<t_p<1$, wherein the progress value $t_p$ represents a ratio of a proportional incubation time period for the consecutively distributed sequence of images of the incubated sample microorganism divided by an overall incubation time period from start to end of the incubation for the respective microorganism, and c) Predicting microorganism growth or microorganism growth inhibition for the incubated sample microorganism as a function of an output score ($S_o$) $0 \leq S_o \leq 1$ of a deep learning neural network configured to extract spatio-temporal features of the sequence of images and to classify the respective images, wherein $S_o=0$ represents a distinct microorganism growth inhibition and $S_o=1$ represents a distinct microorganism growth, and wherein the deep learning neural network uses as input data
   (i) a sequence of pixel intensity ($p_i$) per pixel for the two or more images of step b), or
   (ii) a determined sequence of differences in the pixel intensity ($\Delta p_i$) per pixel between two consecutive images respectively for the two or more images of step b), or
   (iii) a sequence of pixel intensity ($p_i$) per pixel for the two or more images of step b) and a determined sequence of differences in the pixel intensity ($\Delta p_i$) per pixel between two consecutive images respectively for the two or more images of step b).

A second aspect of the present invention relates to a rapid antimicrobial susceptibility testing system for predicting microorganism growth or microorganism growth inhibition of a microorganism inoculum in a phenotypic antimicrobial susceptibility test (AST), the system comprising or consisting of:

a) an incubation assembly configured for housing an incubation device for incubating a sample of a microorganism with a single antimicrobial agent or a combination of antimicrobial agents, b) an imaging device configured to taking a sequence of two or more digital images of the incubated sample microorganism of feature a) on the incubating device, wherein the imaging device is configured to provide information on pixel intensity ($p_i$) per pixel for each image and wherein the imaging device is further configured to taking the sequence of images consecutively distributed within a progress value ($t_p$) with $0<t_p<1$, wherein the progress value $t_p$ represents a ratio of a proportional incubation time period for the consecutively distributed sequence of images of the incubated sample microorganism divided by an overall incubation time period from start to end of the incubation for the respective microorganism, and c) a computer assembly comprising one or more processors, and an analysis module comprising a deep neural network unit configured to extract spatio-temporal features of the sequence of images and to classify the respective images and one or more computer-readable media storing instructions that, when executed by the one or more processors, cause the one or more processors to perform predicting microorganism growth or microorganism growth inhibition for the incubated sample microorganism as a function of an output score ($S_o$) $0 \leq S_o \leq 1$ of the deep learning neural network, wherein $S_o=0$ represents a distinct microorganism growth inhibition and $S_o=1$ represents a distinct microorganism growth, and wherein the deep learning neural network is configured to use as input data
   (i) a sequence of pixel intensity ($p_i$) per pixel for the two or more images of feature b), or
   (ii) a determined sequence of differences in the pixel intensity ($\Delta p_i$) per pixel between two consecutive images respectively for the two or more images of feature b), or
   (iii) the sequence of pixel intensity ($p_i$) per pixel for the two or more images of feature b) and a determined sequence of differences in the pixel intensity ($\Delta p_i$) b per pixel between two consecutive images respectively for the two or more images of feature b).

A third aspect of the present invention relates to the use of a deep neural network unit configured to extract spatio-temporal features of a sequence of two or more images of an incubated sample of microorganism and to classify the respective images for predicting microorganism growth or microorganism growth inhibition of the incubated sample microorganism as a function of an output score ($S_o$) $0 \leq S_o \leq 1$ of the deep learning neural network, wherein $S_o=0$ represents a distinct microorganism growth inhibition and $S_o=1$ represents a distinct microorganism growth, characterized in that the sequence of images is consecutively distributed within a progress value ($t_p$) with $0<t_p<1$, wherein the progress value $t_p$ represents a ratio of a proportional incubation time period for the consecutively distributed sequence of images of the incubated sample microorganism divided by an overall incubation time period from start to end of the incubation for the respective microorganism, and wherein the deep learning neural network is configured to use as input data (i) a sequence of pixel intensity ($p_i$) per pixel for the two or more images of the incubated sample microorganism of feature b), or (ii) a determined sequence of differences in the pixel intensity ($\Delta p_i$) per pixel between two consecutive images respectively for the two or more images of feature b), or (iii) the sequence of pixel intensity ($p_i$) per pixel for the two or more images of the incubated sample microorganism of feature b) and a determined sequence of differences in the pixel intensity ($\Delta p_i$) per pixel between two consecutive images respectively for the two or more images of feature b).

The inventive aspects of the present invention as disclosed hereinbefore can comprise—in case it is reasonable for a person skilled in the art—any possible combination of the preferred inventive embodiments as set out in the dependent claims or disclosed in the following detailed description including the experimental section.

BRIEF DESCRIPTION OF DRAWINGS

Further aspects, characteristics and advantages of the invention will ensue from the following description of the embodiments with reference to the accompanying drawings, wherein

FIGS. 2*a*), 2*b*), 2*c*) respectively represent a schematic view on the deep learning neural network models 1 (FIG. 2*a*)), 2 (FIG. 2*b*)) and 3 (FIG. 2*c*)) to be inventively used without progress value as input data.

FIGS. 8*a*), 8*b*) represent a histogram of prediction of microorganism growth 1 or microorganism inhibition (0) for a respective test set at progress value 0.2 (FIG. 8*a*)) and a respective confusion matrix (FIG. 8*b*)).

FIGS. 9*a*), 9*b*) represent a histogram of prediction of microorganism growth 1 or microorganism inhibition (0) for a respective test set at progress value 0.4 (FIG. 9*a*)) and a respective confusion matrix (FIG. 9*b*)).

DETAILED DESCRIPTION OF EMBODIMENTS

Figure 1:
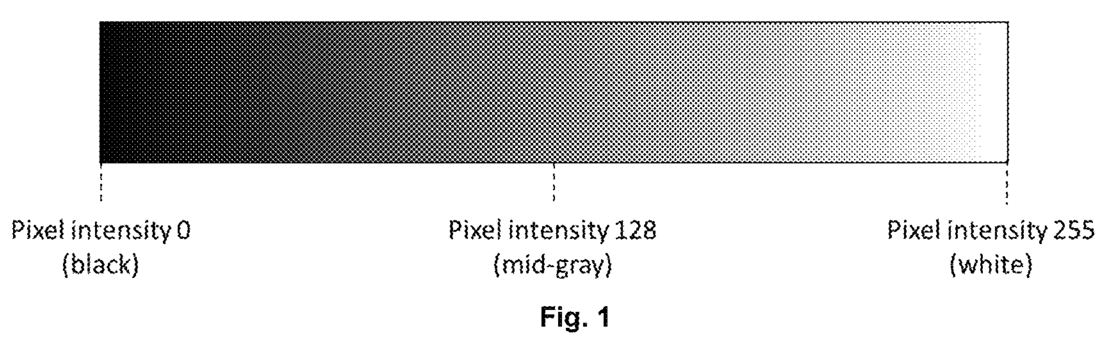
FIG. 1 represents for 8-bit depth pixels a general pixel intensity greyscale for a single-channel image in the range of 0 to 255.

As described in detail below, the present inventors have unexpectedly found out that it is possible to provide a prediction of microorganism growth or microorganism growth inhibition of a microorganism inoculum in a phenotypic antimicrobial susceptibility test (AST) in real time and below the overall standard incubation period for the respective microorganism, when using a deep neural network unit configured to extract spatio-temporal features of a sequence of two or more images of an incubated sample and to classify the respective images, wherein the sequence of images is consecutively distributed within a progress value ($t_p$) with $0<t_p<1$ and wherein the progress value $t_p$ represents a ratio of a proportional incubation time period for the consecutively distributed sequence of images of the incubated sample microorganism divided by an overall incubation time period from start to end of the incubation for the respective microorganism, and in case the deep learning neural network is configured to use as input data (i) a sequence of pixel intensity ($p_i$) per pixel for the two or more, preferably eight or more, more preferably 16 or more images of the incubated sample microorganism of feature b), or (ii) a determined sequence of differences in the pixel intensity ($\Delta p_i$) per pixel between two consecutive images respectively for the two or more, preferably eight or more, more preferably 16 or more images of feature b), or (iii) the sequence of pixel intensity ($p_i$) per pixel for the two or more, preferably eight or more, more preferably 16 or more images of the incubated sample microorganism of feature b) and a determined sequence of differences in the pixel intensity ($\Delta p_i$) per pixel between two consecutive images respectively for the two or more, preferably eight or more, more preferably 16 or more images of feature b).

Optionally, the deep neural network additionally uses as input data (iv) the respective progress value $t_p$ used in (i), (ii) or (iii), wherein in (iii) the same progress value $t_p$ is used, and/or (v) information on the antimicrobial agent present in the incubated sample in step a) and/or (vi) information on the microorganism present in the incubated sample in step a).

In the context of the present invention, the term "sample" or "incubated sample" is used to represent a separated sample composition of a microorganism, which is incubated under suitable incubation conditions (suitable incubation excipients and suitable incubation carrier, such as incubation chamber) in such a way that a sequence of two or more, preferably eight or more, more preferably 16 or more digital images can be taken during the applicable progress. Thus, with respect to all aspects and embodiments of the present invention in particular two, three, four, five, six, seven, eight, nine, ten, eleven, twelve, thirteen, fourteen, fifteen, sixteen or more images are taken of the respective sample or incubated sample and are used as input data in the respective inventive deep learning neural network.

According to the present invention, the image of the incubated sample is configured to provide information on pixel intensity ($p_i$) per pixel per image. The image of the incubated sample may preferably comprise 24×24 pixels. Based on this information on pixel intensity ($p_i$), differences in the pixel intensity ($\Delta p_i$) per pixel per image in relation to the subsequent image in the sequence of images may be determined. This determination may be conducted with suitable means, preferably with suitable computing assembly, more preferably the computing assembly, which also comprises the deep learning neural network.

In the context of the present invention, the expression "pixel intensity ($p_i$)" relates to the intensity of a pixel as a single value denoting the relative brightness of the said pixel in one channel. As an example for single-channel images (grey level images), the pixel intensity has only one value, while pixel intensity in a three-channel image (colour image, such as RBG) has one value for each channel RBG colour, thus three values. The pixel intensity for the majority of digital cameras having 8-bit depth pixels generally ranges from 0 to 255, while for some digital cameras offering 16-bit depth, the pixel intensity generally ranges from 0 to 65,535. Typically the value zero represents black (ideal darkness) and 255 represents white (saturated brightness) as shown in FIG. 1 displaying the pixel intensity scale for 8-bit depth pixels. A greyscale image may also comprise pixel intensities inbetween 0 and 255, e.g., a mid-grey colour would be realized with pixel intensity 128. Thus, pixel intensity values inbetween 0 to 255 represent various shades of grey. With respect to the present invention single-channel images with 8-bit depth are preferably used in view of data size.

Furthermore, the inventive method, system and use are improved over the prior art, as the input data for the deep learning neural network does not require the use of high resolution images having a spatial resolution of <0.01 mm/pixel, as provided by holographic microscopes used the prior art. In contrast, the present invention may preferably use images having a spatial resolution in the range of 0.1 to 0.01 mm/pixel, more preferably 0.075 mm/pixel or 0.05 mm/pixel, as only the information on pixel intensity ($p_i$) per pixel of the image is relevant in order to provide the accelerated access to the AST information and not the structure/shape of microorganism colonies overtime. In case, however, an image to be used for the present invention provides a spatial resolution <0.01 mm/pixel, the image may preferably be preprocessed prior to be used as input data for the deep neural network to exhibit a spatial resolution in the range of 0.1 to 0.01 mm/pixel, preferably 0.075 mm/pixel or 0.05 mm/pixel. In case the image may not be preprocessed, it is preferred to adapt the training of the deep neural network respectively, e.g. by using respective high spatial resolution images as training data.

Furthermore, the inventive method, system and use may provide a possibility for tuning the trade-off between sensitivity and specificity by adapting the training data and/or predetermining an output score threshold $S_T$. Moreover, the inventive method, system and use may be less sensitive and, thus, more robust, in view of processing anomalies, such as air bubbles etc., as a sequence of images covering a time period is used. In addition, the inventive method, system and use may provide suitable performance metrics even when using input data provided by a different system than the training data as set out in the experimental section in detail.

Furthermore, the present invention is in particular applicable for real-time, high-throughput test screenings of a large array of samples (e.g. >1,000 incubation chambers, preferably e.g., 1,500 or 3,000 incubation chambers with respective samples), as the present invention pays attention to the pixel intensity ($p_i$) of the respective incubated sample images, and not to the structure/shape of microorganism colonies during incubation.

The present invention is based on the use of a deep learning neural network for predicting the microorganism growth or no growth for the respective incubated sample images (signal prediction/feature prediction), wherein the deep learning neural network is configured to extract spatio-temporal features of a sequence of two or more digital images of an incubated sample microorganism and to classify the respective images. The sequence of images is consecutively distributed within a progress value ($t_p$) with $0<t_p<1$, wherein the progress value $t_p$ represents a ratio of a proportional incubation time period for the consecutively distributed sequence of images of the incubated sample microorganism divided by an overall incubation time period from start to end of the incubation for the respective microorganism. In other words, the present invention also allows to process an image sequence from arbitrary time frames of the incubation time.

The expression "proportional incubation time period for the consecutively distributed sequence of images of the incubated sample microorganism", thus, refers to the time period of the actual incubation time, which is used for analyzing the image data accordingly and may alternatively be called "analyzing time", "analyzing time period", or "running time".

In contrast thereto, the expression "overall incubation time period from start to end of the incubation for the respective microorganism" relates to the standard incubation time to be generally conducted for phenotypical AST of the respective microorganism.

In case the analysis time period would take longer than the overall incubation time period, the progress value would be clipped to $t_p=1$ at maximum.

As an example, in case the progress value represents $t_p=0.5$, the proportional incubation time period for the consecutively distributed sequence of images of the incubated sample microorganism and, thus, the analysis time represents half of the overall standard incubation time for a respective microorganism. Within this proportional incubation time period the sequence of images is consecutively, preferably evenly, distributed, i.e. the first image of the sequence is taken after the start of incubation and the last image of the sequence is taken before the time point of the progress value $t_p=0.5$. In other words, in case the standard incubation time is 20 hours, the progress $t_p=0.5$ means, that the images are consecutively distributed within the start of the incubation (0) and the first 10 hours of incubation time, wherein at start of incubation and at 10 hours no images are taken.

In connection with the present invention, the expression "signal classification"/"feature classification"/"sequence of images classification" relates to the training phase and represents a prediction of whether a sequence of images of a sample microorganism used in training (also "training sample microorganism") shows a microorganism growth (class 1) or a microorganism growth inhibition (class 0), wherein the signal classification is taken using the complete set of input features covering the whole incubation time. In other words, based on the complete set of input data covering the whole incubation time, the particular set of sequence of images is classified to indicate microorganism growth or microorganism growth inhibition in training phase.

In connection with the present invention, the expression "signal prediction"/"feature prediction"/"sequence of images prediction" is generally used in validation and test phase and represents a prediction of whether a sequence of images of a sample microorganism shows a microorganism growth (class 1) or a microorganism growth inhibition (class 0), wherein the prediction is taken using an incomplete set of input features covering only part of the whole incubation time, namely covering the time period relating to the corresponding progress value $t_p$. In other words, the inventive method of predicting microorganism growth or microorganism growth inhibition of a microorganism inoculum in a phenotypic antimicrobial susceptibility test (AST) is based on an incomplete set of images. Accordingly, the inventive method enables providing earlier access to the AST information. Furthermore, as substantially no time lag between image taking and prediction of deep neural network exists, the inventive method provides online results.

In connection with the present invention, the expression "may"/"can" etc. with reference to the optional application on an embodiment also includes the meaning of the actual application of this embodiment.

In FIGS. 2*a*) to 2*c*) the deep learning neural network (10) to be used for predicting the microorganism growth or no growth according to the present invention is schematically displayed, wherein the deep learning neural network (10) is configured to extract spatio-temporal features and to classify the respective images in suitable layers, wherein the network (10) uses as input data (i) a sequence in pixel intensity ($p_i$) per pixel for the two or more, preferably eight or more, more preferably 16 or more images (in the following called model 1, see also FIG. 2*a*)), or (ii) a determined sequence of differences in the pixel intensity ($\Delta p_i$) per pixel between two consecutive images respectively for the two or more, preferably eight or more, preferably 16 or more images (in the following called model 2, see also FIG. 2*b*)), or (iii) a sequence in pixel intensity ($p_i$) per pixel for the two or more, preferably eight or more, preferably 16 or more images and a determined sequence of differences in the pixel intensity ($\Delta p_i$) per pixel between two consecutive images respectively for the two or more, preferably eight or more, more preferably 16 or more images (in the following called model 3, see also FIG. 2*c*)).

Figure 3:
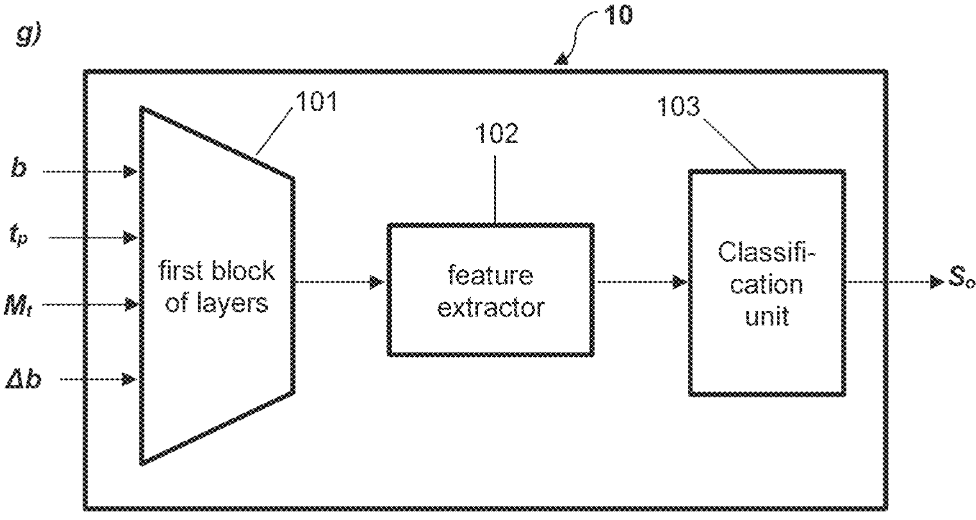
FIGS. 3*a*) to 3*g*) respectively represent a schematic view on the deep learning neural network models 1 (FIGS. 3*a*) and 3*d*)), 2 (FIGS. 3*b*) and 3*e*)) and 3 (FIGS. 3*c*), 3*f*) and 3*g*)) to be inventively used with progress value as input data and optionally information on the antimicrobial agent and optionally the microorganism.

In FIGS. 3*a*) to 3*g*) a preferred embodiment of the present invention is disclosed, wherein (iv) the respective progress value $t_p$ used in (i), (ii) or (iii) is used as additional input data, wherein in (iii) the same progress value $t_p$ is used.

The additional use of the respective progress value $t_p$ is advantageous in order to reduce the risk of false negative predictions (prediction of microorganism growth inhibition), in particular when the progress value is small and/or when using slow growing microorganisms, or false positive predictions (prediction of microorganism growth), in particular when the progress value is high and/or when using fast growing microorganisms.

According to one embodiment of the present invention, the progress value $t_p$ is concatenated in later layers of the deep learning neural network with the already condensed information of the pixel intensities, preferably in the layer(s) connected to the classification layers (fully connected layers), so that it can exhibit more weight for adapting the classification (see FIGS. 3*a*) to 3*f*).

According to an additive or alternative preferred embodiment, the input data may also contain information on the antimicrobial agent used in a respective well and optionally the microorganism of the sample present in the respective well (see FIGS. 3*d*) to 3*g*)).

This additional input data may be used in form of a vector information ($M_v$) on the antimicrobial agent used in a respective well and optionally a vector ($M_v$) containing information on the microorganism of the sample present in the respective well. The respective vectors may be built as follows. If there are n antimicrobial agents considered, the vector for antimicrobial agents has n+1 fields. Each field represents a single antimicrobial agent and the last field represents the information "no antimicrobial agent present in the well". For each well, only one of the vector fields exhibits the value 1, representing the respective antimicrobial agent type or "no antimicrobial agent present in the well", whereas the remaining vector fields exhibit the value 0. In analogous way, the vector containing information on the microorganism of the sample is built. Accordingly, if there are n microorganisms considered, the vector for microorganism in the sample has n+1 fields. Each field represents a single microorganism and the last field represents the information "no microorganism present in the well". For each well, only one of the vector fields exhibits the value 1, representing the respective microorganism type or "no microorganism present in the well", whereas the remaining vector fields exhibit the value 0.

According to one embodiment of the present invention, the respective vector information ($M_v$) may be concatenated in later layers of the deep learning neural network with the already condensed information of the pixel intensities, preferably in the layer(s) connected to the classification layers (fully connected layers), so that it can exhibit more weight for adapting the classification (see FIGS. 3*d*) to 3*f*).

According to an alternative embodiment of the present invention, the progress value $t_p$ and the information on antimicrobial agent and preferably the microorganism of a respective well is concatenated in an earlier block of layers, such as block 101, of the deep learning neural network (see FIG. 3*g*)). The input data is preferably aggregated into a three-dimensional matrix, in particular a "tensor", wherein this tensor (also "single data sample") comprises or consists of the information of the sequence of pixel intensity ($p_i$) per pixel for the two or more, preferably eight or more, more preferably 16 or more images of the incubated sample microorganism in the well (b) and a determined sequence of differences in the pixel intensity ($\Delta p_i$) per pixel between two consecutive images ($\Delta$b) respectively for the two or more, preferably eight or more, more preferably 16 or more images of the incubated sample microorganism in the well as well as the value of the time progress $t_p$ and the information on antimicrobial agent and preferably the microorganism of the respective well respectively in form of a matrix ($M_t$), wherein each of the n+1 fields of the vector is a matrix, preferably a 24×24 matrix, and in case the antimicrobial agent is present in the well, the matrix is full of ones. In case of using 72 antimicrobial agents and 12 bacteria types as microorganisms tested in a well using a 24×24 matrix, a single input sample is a tensor in three-dimensional form of size 117×24×24. Due to the change of the vector size n+1 of the information on antimicrobial agent and preferably the microorganism of the respective well into a three-dimensional matrix format ($M_t$) without addition of any further information, the provided information in a single data sample may be in part redundant. Nevertheless, the use of input data having a three-dimensional matrix allows using a simpler CNN, which may not need to be changed in case new features may be added to the input data. So, the three-dimensional CNN model may be regarded as more robust in view of further input data changes and/or may be regarded more universal.

The use of the information on the antimicrobial agent used in the respective well and optionally the microorganism present in the respective well may also reduce the risk of

- false negative predictions (prediction of microorganism growth inhibition), such as when using slow growing microorganisms, or
- false positive predictions (prediction of microorganism growth), in particular when using fast growing microorganisms.

In the context of the present invention, fast (or rapid) growing microorganisms are defined to represent microorganisms that change macroscopic characteristics of the culturing medium (such as change of turbidity, viscosity, colour, formation of visible colonies) after overnight culturing in optimal conditions. As an example fast (or rapid growing microorganisms include: *Escherichia coli, Staphylococcus aureus, Pseudomonas aeruginosa, Klebsiella pneumoniae, Enterococcus faecalis* (also known as *Streptococcus faecalis*). They typically require 16-24 hours of culturing, according to CLSI standards.

In the context of the present invention, slow growing microorganisms—in contrast to fast growing microorganisms—are defined to not change macroscopic characteristics (such as change of turbidity, viscosity, colour, formation of visible colonies) after overnight culturing either when applying optimal conditions or when applying non optimal conditions. Accordingly, fast growing microorganisms may also be regarded as slow growing microorganisms in the context of the present invention, in case their growth rate specifically depends on the incubation conditions and the incubation conditions are not optimal. Thus, slow growing microorganisms can generally also be regarded as fastidious, i.e. they require specific culturing medium and environment. Accordingly, slow growing microorganisms may include various mycobacteria strains, such as *Mycobacterium tuberculosis, Mycobacterium alsiense, Mycobacterium celatum, Mycobacterium gordonae, Mycobacterium haemophilum, Mycobacterium kyorinense, Mycobacterium malmoense, Mycobacterium simiae* complex, *Mycobacterium szulgai, Mycobacterium terrae* complex (such as *Mycobacterium triviale, Mycobacterium nonchromogenicum*, and *Mycobacterium terrae*), *Mycobacterium ulcerans*, and *Mycobacterium xenopi*, in particular including oligotroph species in soil or copiotroph species in soil.

Both abovementioned cases (preventing false negative and preventing false positive) may be generally described as obtaining better classification results due to the use of microbial and antimicrobial agents' information. Various types of microorganisms such as bacteria may have various characteristics of growth in time. In connection with the present invention "characteristics of growth in time" or "growth in time characteristics" refers to the size of the microorganism colony, such as bacterial colony, as a function of time. For some types of microorganisms such as bacteria, the growth is intense and the colony is densely packed, which results in higher light scattering. For other types of microorganisms such as bacteria, the growth is less intense in time. For again other types of microorganisms such as bacteria, the growth starts from several tiny colonies which later join to create one greater colony. For again other types of microorganisms such as bacteria, the growth starts from one single colony which grows in time.

The growth of the microorganism such as bacteria itself can be regarded as one issue, which may have an impact on the light scattering and, thus, on the result. The interaction between the microorganism type such as bacteria type and antimicrobial type such as antibiotic type can be regarded as a second issue. The growth (or growth inhibition) of the microorganism such as bacteria may be different due to the antimicrobial such as antibiotic used. The antibiotics may generally be divided into two groups dependent on their functional objectives: The functional objective of germicidal antibiotics may be regarded to destroy bacteria, whereas the functional objective of bacteriostatic antibiotics may be regarded to prevent/inhibit the growth of bacteria.

In connection with the present invention, a sample treated with an bacteriostatic antibiotic may be regarded (labeled) "no growth" even in case the bacteria comprised in the sample may exhibit a small negligible growth until end of the respective incubation in comparison to a full growth exhibited in a sample not treated with an antimicrobial. For example, with respect to Trimethoprim and Trimethoprim-sulfamethoxazole as bacteriostatic antibiotic, the maximum negligible growth to be labeled "no growth" is regulated by the EUCAST reading guide for broth microdilution, version 2.0, March 2020, and amounts up to 20% in comparison to a full growth exhibited in a sample not treated with the respective bacteriostatic antibiotics. With respect to Ciprofloxacin and Levofloxacin, no respective guidelines presently apply; in the absence of such regulations the maximum growth according to the present invention to be labeled "no growth" amounts up to 25% for Ciprofloxacin in comparison to a full growth exhibited in a sample not treated with the respective bacteriostatic antibiotic. With respect to Levofloxacin, the maximum negligible amount of growth to be labeled "no growth" amounts up to 30% in comparison to a full growth exhibited in a sample not treated with the respective bacteriostatic antibiotic. In other words, if bacteria grow to such an extend as to create a negligible small colony persisting until the end of the incubation, then it labeled as "no-growth" in in comparison to "full growth" as seen in untreated samples where the colony grow and occupy a larger well area at the end of the incubation time.

In connection with the present invention, a sample treated with a germicidal antibiotic may be regarded (labled) "no growth" in case no bacterial colony can be detected at the end of incubation time.

Thus, the interaction between the bacteria type and antibiotic type results in different characteristics of growth in time. Accordingly, adding antimicrobial agent and bacteria information to the inventive CNN allows to adjust weights in the network for particular case of microbial, antimicrobial or microbial-antimicrobial pair. In other words, providing information on the microbial and/or antimicrobial agents results in that the weights are better adjusted to differentiate between growth and no-growth cases where "growth" and "no-growth" for different types of pairs may be defined in a differently.

According to the present invention, the classification results may be improved in case

- information of following bacteria selected from the group consisting of *Acinetobacter* such as *Acinetobacter baumannii, Staphylococcus* such as *Staphylococcus aureus* and *Staphylococcus epidermidis*, Enterobacterales such as Enterobacteriaceae, Erwiniaceae, Hafniaceae, Morganellaceae, and Yersiniaceae, *Pseudomonas* such as

*Pseudomonas aeruginosa*, and *Enterococcus* such as *Enterococcus faecalis*, and *Enterococcus faecium* is used for all aspects and embodiments of the present invention and/or information on the following antimicrobial agents/antibiotics selected from the group consisting of minocycline, piperacillin, tazobactam, meropenem, imipenem, trimethoprim, sulfamethoxazole, tetracycline, cefalexin, nitrofurantoin, amoxicillin, clavulanic acid, ceftazidime, avibactam, oxacillin, cefepime, ampillicin, sulbactam, ciprofloxacin, ofloxacin, doxycycline, ticarcillin, moxifloxacin, norfloxacin, ceftriaxone, amikacin, levofloxacin, nenzylpenicillin, chloramphenicol, cefuroxime, cefotaxime, erythromycin, tedizolid, vancomycin, cefoxitin, gentamicin, tobramycin, and cefazolin or mixtures thereof such as the combination of piperacillin and tazobactam and the combination of trimethoprim and sulfamethoxazole, preferably, wherein the information on the following antimicrobial agents/antibiotics minocycline, meropenem, imipenem, cefalexin, nitrofurantoin, ceftazidime, cefepime, vancomycin, the combination of piperacillin and tazobactam or the combination of trimethoprim and sulfamethoxazole is used for all aspects and embodiments of the present invention.

In particular in case the following microbial-antimicrobial pairs are used in the sample, it may be advantageous to additionally use the information of the microbial and/or, preferably and the information of the antimicrobial for all aspects and embodiments of the present invention in order to improve the classification results:

| Antimicrobial/antibiotic | Microbial/Bacteria |
|---|---|
| Minocycline | *Acinetobacter* |
| Piperacillin-tazobactam | *Acinetobacter* |
| Meropenem | *Acinetobacter* |
| Imipenem | *Acinetobacter* |
| Trimethoprim-sulfamethoxazole | *Staphylococcus* |
| Tetracycline | *Acinetobacter* |
| Cefalexin | *Enterobacterales* |
| Imipenem | *Enterobacterales* |
| Nitrofurantoin | *Enterobacterales* |
| Amoxicillin-clavulanic acid | *Enterobacterales* |
| Minocycline | *Enterobacterales* |
| Ceftazidime | *Staphylococcus* |
| Trimethoprim-sulfamethoxazole | *Enterobacterales* |
| Oxacillin | *Staphylococcus* |
| Cefepime | *Pseudomonas* |
| Meropenem | *Enterobacterales* |
| Tetracycline | *Enterobacterales* |
| Ampicillin-sulbactam | *Enterobacterales* |
| Imipenem | *Pseudomonas* |
| Trimethoprim | *Enterobacterales* |
| Cefepime | *Enterobacterales* |
| Cefepime | *Staphylococcus* |
| Ciprofloxacin | *Staphylococcus* |
| Ofloxacin | *Staphylococcus* |
| Trimethoprim | *Staphylococcus* |
| Doxycycline | *Acinetobacter* |
| Ticarcillin-clavulanic acid | *Staphylococcus* |
| Moxifloxacin | *Pseudomonas* |
| Ceftazidime-avibactam | *Staphylococcus* |
| Doxycycline | *Staphylococcus* |
| Cefepime | *Acinetobacter* |
| Meropenem | *Pseudomonas* |
| Doxycycline | *Enterobacterales* |
| Ciprofloxacin | *Pseudomonas* |
| Ciprofloxacin | *Enterobacterales* |
| Norfloxacin | *Enterobacterales* |
| Minocycline | *Staphylococcus* |
| Ceftriaxone | *Enterobacterales* |
| Moxifloxacin | *Staphylococcus* |

-continued

| Antimicrobial/antibiotic | Microbial/Bacteria |
|---|---|
| Tetracycline | *Enterococcus* |
| Amikacin | *Enterobacterales* |
| Ciprofloxacin | *Acinetobacter* |
| Ceftriaxone | *Staphylococcus* |
| Ampicillin-sulbactam | *Acinetobacter* |
| Tetracycline | *Staphylococcus* |
| Amikacin | *Acinetobacter* |
| Doxycycline | *Enterococcus* |
| Levofloxacin | *Staphylococcus* |
| Norfloxacin | *Pseudomonas* |
| Benzylpenicillin | *Staphylococcus* |
| Ceftriaxone | *Acinetobacter* |
| Chloramphenicol | *Staphylococcus* |
| Norfloxacin | *Staphylococcus* |
| Amikacin | *Pseudomonas* |
| Cefuroxime iv | *Staphylococcus* |
| Cefotaxime | *Acinetobacter* |
| Erythromycin | *Enterococcus* |
| Tedizolid | *Staphylococcus* |
| Amoxicillin-clavulanic acid | *Enterococcus* |
| Norfloxacin | *Enterococcus* |
| Trimethoprim-sulfamethoxazole | *Acinetobacter* |
| Ceftazidime | *Acinetobacter* |
| Moxifloxacin | *Enterobacterales* |
| Vancomycin | *Enterococcus* |
| Nitrofurantoin | *Staphylococcus* |
| Cefotaxime | *Staphylococcus* |
| Meropenem | *Staphylococcus* |
| Ticarcillin-clavulanic acid | *Acinetobacter* |
| Cefoxitin | *Enterobacterales* |
| Cefotaxime | *Enterobacterales* |
| Levofloxacin | *Acinetobacter* |
| Ampicillin | *Enterobacterales* |
| Levofloxacin | *Enterobacterales* |
| Piperacillin | *Acinetobacter* |
| Gentamicin | *Pseudomonas* |
| Tobramycin | *Pseudomonas* |
| Tobramycin | *Acinetobacter* |
| Ampicillin | *Staphylococcus* |
| Cefazolin | *Staphylococcus* |
| Ceftriaxone | *Pseudomonas* |
| Erythromycin | *Staphylococcus* |
| Imipenem | *Staphylococcus* |
| Piperacillin | *Staphylococcus* |
| Vancomycin | *Staphylococcus* |

In particular, a very significant increase in specificity has been observed for the following pairs in case of using microbial and antimicrobial information for all aspects of the present invention:

| Antimicrobial/antibiotic | Microbial/Bacteria |
|---|---|
| Minocycline | *Acinetobacter* |
| Piperacillin-tazobactam | *Acinetobacter* |
| Meropenem | *Acinetobacter* |
| Trimethoprim-sulfamethoxazole | *Staphylococcus* |
| Cefalexin | *Enterobacterales* |
| Imipenem | *Enterobacterales* |
| Nitrofurantoin | *Enterobacterales* |
| Ceftazidime | *Staphylococcus* |
| Imipenem | *Pseudomonas* |
| Cefepime | *Enterobacterales* |
| Vancomycin | *Enterococcus* |

In the preferred embodiment, when using the progress value $t_p$ as additional input data, the inventive method, system and use additionally uses the information on time of incubation in order to provide weights for the images as input data. This means that the deep learning system learns to apply for a short progress value appropriate weights already on a slightest trend of pixel intensity increase. In other words, the inventive system learns to be more sensitive for positive incubation cultures at shorter progress values $t_p$ in order to avoid false negative predictions. In addition, when applying a higher progress value $t_p$, an appropriate weight is applied only in case the pixel intensity increase is substantive. In other words, the inventive system learns to be less sensitive for positive incubation cultures at higher progress value in order to avoid false positive predictions. In summary, the progress value $t_p$ may be regarded to represent a scalar inverted proportional to the microorganism growth/growth inhibition classification.

Accordingly, in an additional or alternative preferred embodiment, when using the information on antimicrobial agent and optionally on microorganism type of the respective incubated sample (well) either in vector ($M_v$) format n+1 as additional input data or in a matrix format as additional input data to be aggregated into a three-dimensional tensor format, the inventive method, system and use may additionally use information about the specific growing information of antimicrobial agents and optionally microorganism types in order to provide weights for the images as input data. This means that the deep learning system learns to apply for those antimicrobial agents and microorganisms, which may be prone to false negative/false positive results appropriate respective weights on the trend of pixel intensity increase.

In other words, the inventive deep learning system applies the knowledge on the microbial and antimicrobial agent in such a way during the training phase that it can modify its internal connections for better discrimination of the growth/no-growth prediction (to minimize the number of incorrectly classified samples). Thus, additional data relating to microbial present in the sample and/or antimicrobial and/or growth information used for the images (called above also weights for the images) plays a vital role in the training phase as the inventive deep learning system learns to apply different classification rules for different type samples (samples with different weights). For instance, if a bacteria of type A grows at the beginning of the incubation regardless of the antibiotic presence, and the inhibition occurs during later phase, and bacteria of type B is inhibited from the very start of the incubation (which finds its representation in different trends of pixel intensities), then such additional input allows the inventive deep learning system to differentiate between these two cases and apply different classification rules (specific weights of its internal connections) for these two cases. This results in lower number of false positive and false negative predictions. Therefore, sensitivity and specificity measures are higher and the deep learning solution may regarded as more reliable.

Figure 4A:
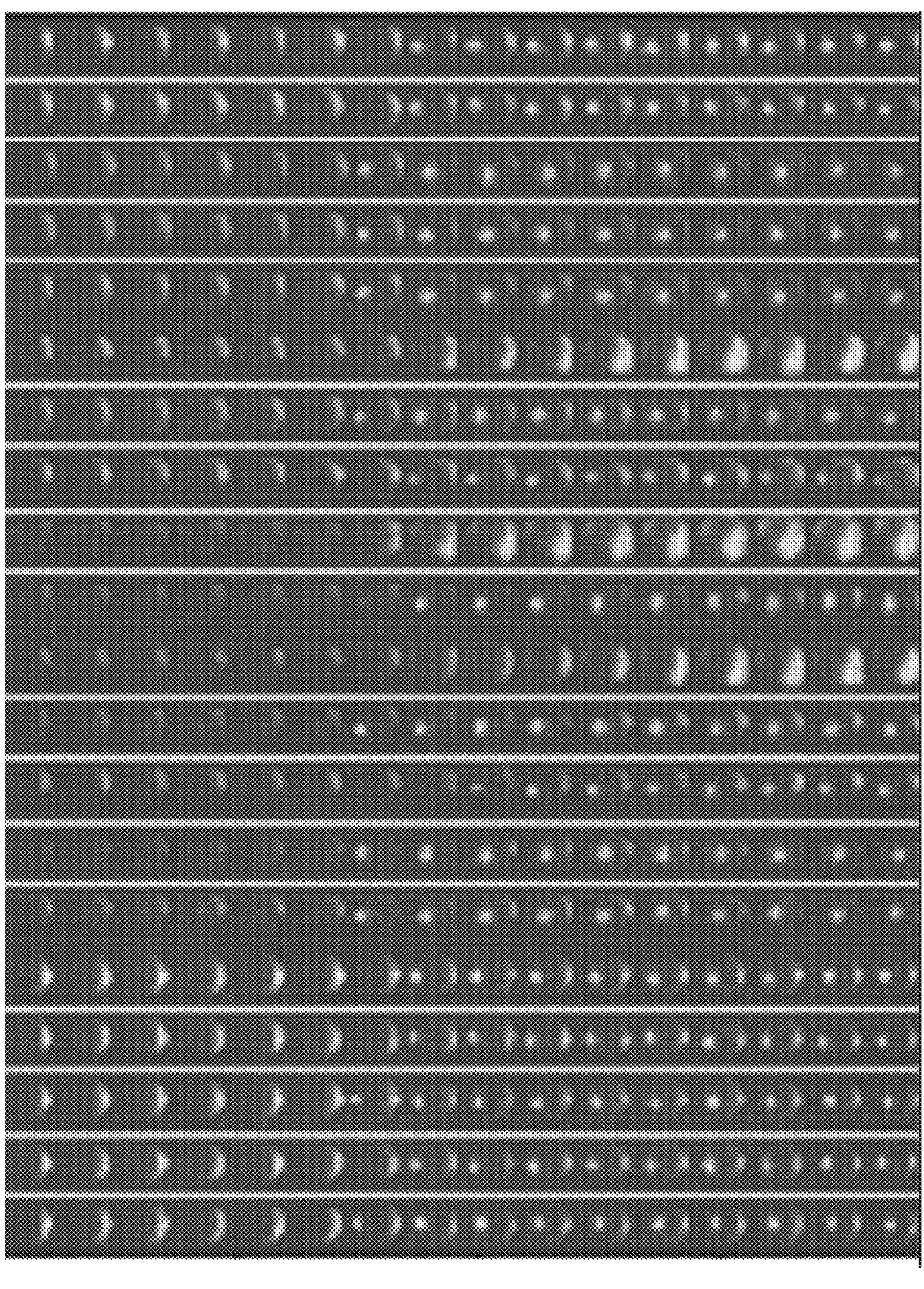
FIGS. 4*a*), 4*b*) respectively represent pixel intensities as input data for 20 exemplary sequences of 16 images taken from a single incubated sample respectively during the respective progress value, wherein FIG. 4*a*) shows 20 sequences of respectively 16 images labelled as microorganism growth inhibition (label 0), and FIG. 4*b*) shows 20 sequences of respectively 16 images labelled as microorganism growth (label 1).
Figure 4B:
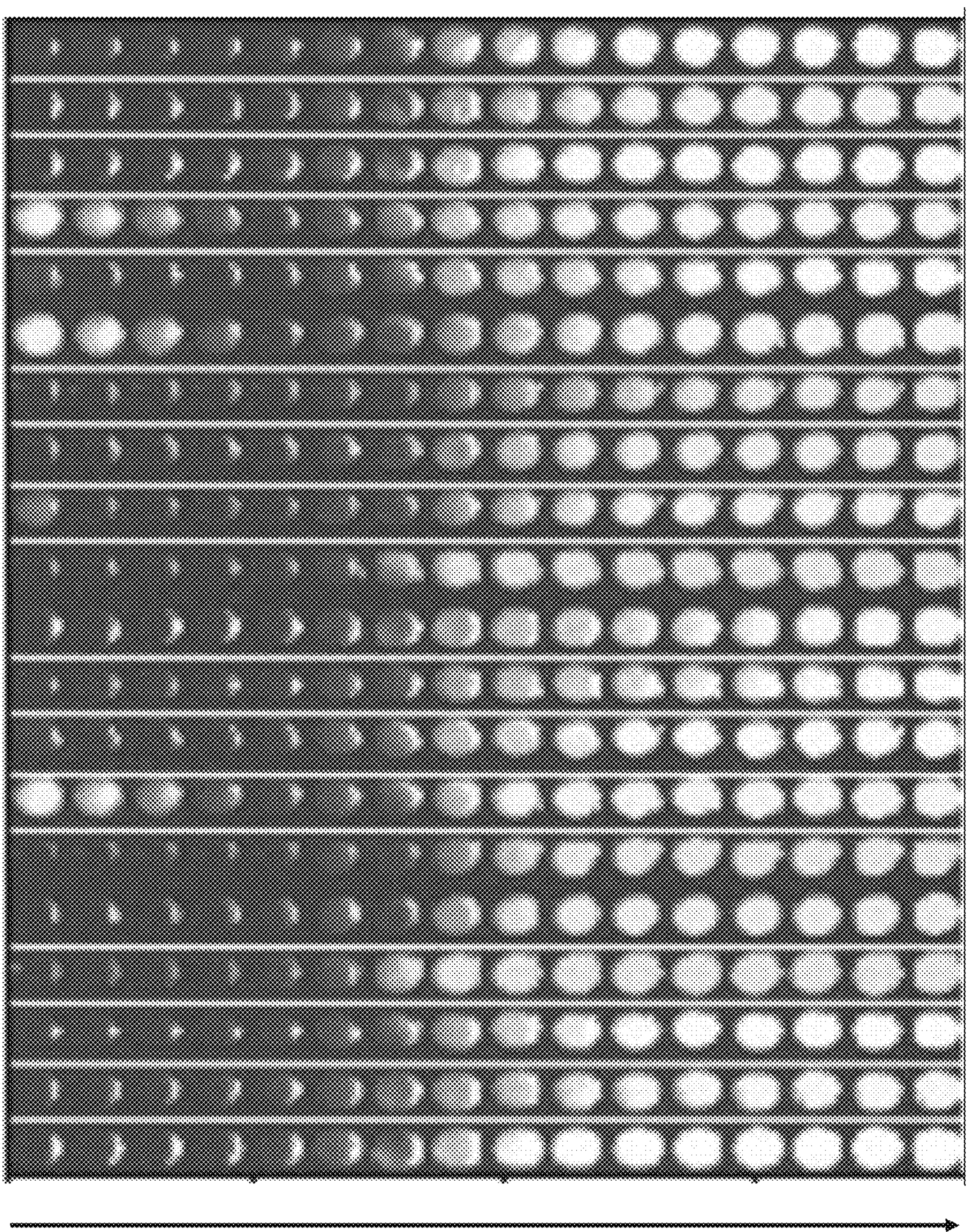

In FIGS. 4*a*) and 4*b*) respective pixel intensities as input data for 20 exemplary sequences of 16 images (each line represents a stacked sequence of 16 (mini) images) taken over incubation time t from a respectively incubated sample during the respective progress value are displayed, wherein FIG. 4*a*) shows 20 sequences of respectively 16 (mini) images labelled as microorganism growth inhibition (label 0), and FIG. 4*b*) shows 20 sequences of respectively 16 (mini) images labelled as microorganisms growth (label 1). In other words, FIGS. 4*a*) and 4*b*) respectively comprise the pixel intensity information of 16 (mini) images taken consecutively and evenly distributed within the respective progress, such that in each line the first image from the left correlates to the image taken at the shortest incubation time of the respective progress value and the last image in the sequence/line (first image from the right) correlates to the image taken at the highest incubation time of the respective progress. The 16 (mini) images in each line are, thus, stacked together to form the sequence of images covering the progress value. When comparing the respective sequences provided in FIGS. 4*a*) and 4*b*) it is apparent that the first images from the left exhibit low pixel intensities. Whereas in FIG. 4*a*) the respective last images of the sequence generally remain to exhibit low pixel intensities correlating to microorganism growth inhibition, the respective last images of the sequences in FIG. 4*b*) show substantively increased pixel intensities in the circular core of the respective images correlating to microorganism growth. In general, the increase in pixel intensity is apparent from the seventh to eighth (mini) image of the respective sequence in FIG. 4*b*). The increased pixel intensities in the first images of the fourth, sixth, and fourteenth sequence (line) in FIG. 4*b*) correlates to artefacts, such as air bubbles etc., which disappear with ongoing incubation time t. The sequence in pixel intensity ($p_i$) per pixel for the two or more, preferably eight or more, more preferably 16 or more images is directly used as feature in models 1 and 3. Not shown in FIGS. 4*a*) and 4*b*) are the determined sequences of differences in the pixel intensity ($\Delta p_i$) per pixel between two consecutive images respectively for the two or more, preferably eight or more, preferably 16 or more images. Such determination of the respective pixel intensity differences preferably takes place as a preprocessing in a part of the analyzing module of the computer assembly of the inventive system.

Figure 5A:
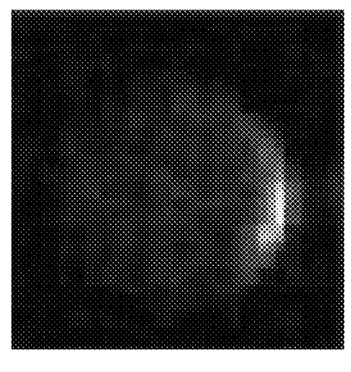
FIGS. 5*a*), 5*b*) represent pixel intensities of an image taken from a single incubated sample as input data (FIG. 5*a*)) and the content of the image in condensed manner in the last fully connected layer of the neural network (FIG. 5*b*).
Figure 5B:
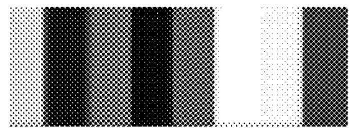
Figure 6A:
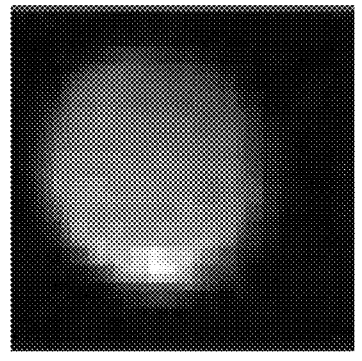
FIGS. 6*a*), 6*b*) represent pixel intensities of an image taken from a single incubated sample as input data (FIG. 6*a*)) and the content of the image in condensed manner in the last fully connected layers of the neural network (FIG. 6*b*).
Figure 6B:
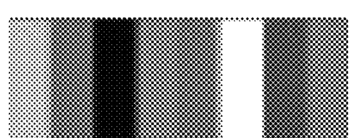

In FIG. 5*a*) and FIG. 6*a*) the respective pixel intensities of one (mini) image taken from a sequence of images of a respective incubated sample as input data, wherein the content of the image in condensed manner as present in the last fully connected layer of the deep learning neural network is respectively displayed in FIGS. 5*b*, 6*b*). FIG. 5 relate to a low pixel intensity (either early time of incubation or no microorganism growth after longer incubation time) and FIG. 6 relate to higher pixel intensities (in particular after longer incubation time of a sample showing microorganism growth).

From FIGS. 4 to 6 it is apparent, that each (mini) image includes a darker surrounding (also called background) of a circular core, wherein the circular core correlates to the pixel intensities of a respective circular incubation chamber of a microtiter plate. In the present case, the background constitutes approximately 40% of the area of every (mini) image, which means that generally only the remaining 60% of the area of every image is used for differentiating positive sequences from negative ones. The pixel intensities of both the background and the circular core can be quantitatively influenced, e.g., by lighting conditions and/different optics. Thus, in order to adapt the deep learning neural network to different lightning conditions and/or different optics as used, e.g., on different rapid antimicrobial susceptibility testing system (also called "machines"), the present invention may preferably use as input data images with acceptable variability taken from systems/machines exhibiting different setups of optics and/or lightning conditions during the training phase of the deep learning neural network images.

As shown in FIGS. 2*a*) to 2*c*) and FIGS. 3*a*) to 3*c*) as well as FIGS. 3*d*) to 3*f*) a first feature extractor (101) may comprise one or more recurrent layers, such as "ConvLSTM2D" layers. "ConvLSTM2D" is a layer providing convolution amended with long short-term memory which is of purpose as subsequent images of wells are ordered in time. This feature extractor uses the respective sequence in pixel intensity ($p_i$) per pixel of the respective images (b) or the respective determined sequence of differences in the pixel intensity ($\Delta p_i$) per pixel between two consecutive images as input data ($\Delta$b). In a second feature extractor (102) comprising one or more Dense layers, the extracted features may be provided in form of a further condensed output data (see FIGS. 5*b*) and 6*b*)). According to the preferred embodiment of the present invention, this condensed output data of the second feature extractor (102) may preferably be concatenated together with the respective progress value $t_p$ as further input data for final prediction in classification unit (103) (see FIGS. 3*a*) to 3*c*) and FIGS. 3*d*) to 3*f*)). In this preferred case, the weights for classification are adapted invers to the progress value $t_p$. With respect to the embodiments of model 3A, as displayed in FIGS. 3*d*) to 3*f*), the respective information of antimicrobial agent and optionally information on microorganism in the respective well may be used in one embodiment in the vector ($M_v$) format n+1 in addition to the respective progress value $t_p$ as further input data to be concatenated in classification unit (103). The weights for classification may be further adapted in regard to the vector $M_v$. In this case, the weights may be adapted inverse or similar to progress value $t_p$ depending on the intensity of microbial/bacteria growth in time. The weights may be adapted in a complex way (some of them increased, some of them decreased) to minimize the loss function of the classifier. The classification unit (103) provides the output score ($S_o$) $0 \leq S_o \leq 1$, wherein $S_o=0$ represents a distinct microorganism growth inhibition and $S_o=1$ represents a distinct microorganism growth. Output scores ($S_o$) $0<S_o<1$ are generally classified as 0 or 1 based on a threshold score $S_T$, wherein the threshold score $S_T$ may be predetermined.

According to an alternative embodiment of the one-model approach (model 3B) shown in FIG. 3*g*) a first block of layers (101) is provided into which input data relating to the respective sequence in pixel intensity ($p_i$) per pixel of the respective two or more images (b) and the respective determined sequence of differences in the pixel intensity ($\Delta p_i$) per pixel between two consecutive images ($\Delta$b), the respective progress value $t_p$ as well as the respective information of antimicrobial agent and optionally information on microorganism in the respective well of the incubated sample preferably in the three-dimensional matrix format ($M_t$) is fed and aggregated into a three-dimensional format. The architecture of the convolutional neural network (CNN) preferably does not consist of recurrent layers, such as "ConvLSTM2D" layers. Instead, the first block of layers (101) into which the input data is fed comprises or consists of a convolutional layer, a batch normalization layer and a ReLU activation layer, preferably in this order. Convolutionals layers are used as convolution is the most widespread operation to extract features from visual images. Pooling layers are used to reduce dimensionality of data. Batch normalization layers are used to prevent overfitting, i.e., to prevent the production of an analysis that corresponds too closely or exactly to the set of data, and may therefore fail to fit to additional data or predict future observations reliably. The purpose of using a ReLU layer is to introduce nonlinearity to the model, wherein nonlinearity being commonly accepted to increase predictive capabilities of the model. Grouping layers into blocks is a common practice in machine learning, however, the number of blocks was found through heuristic testing of the model, i.e., through subsequent training and testing the model comprising subsequent numbers of blocks.

The feature extractor 102 comprises or consists of one block or two, three, four, five or more blocks in series, preferably five blocks in series respectively comprising or consisting of a convolutional layer (*), a batch normalization layer, a ReLU activation function layer, a further convolutional layer, a further batch normalization layer (**), a layer summing the input to the convolutional layer (*) and the output of the further batch normalization layer (), and another ReLU activation function layer, preferably in this order. The classification unit 103** preferably comprises or consists of a convolutional layer, a batch normalization layer, a ReLU activation function layer, a fully connected (dense) layer, and a sigmoid activation layer, preferably in this order. The weights for classification may be further adapted in regard to the vector $M_t$. In this case, the weights may be adapted inverse or similar to progress value $t_p$ depending on the intensity of bacteria growth in time. The weights may be adapted in a complex way (some of them increased, some of them decreased) to minimize the loss function of the classifier.

The inventive block arrangement in the one model approach provides a structure, which is at the same time simple, but at the same time complex enough to provide satisfying classification results. Thus, the presented inventive solution (setup of blocks) may be regarded as highly effective for the presented classification problem.

The classification unit (103) provides the output score ($S_o$) $0 \leq S_o \leq 1$, wherein $S_o=0$ represents a distinct microorganism growth inhibition and $S_o=1$ represents a distinct microorganism growth. Output scores ($S_o$) $0<S_o<1$ are generally classified as 0 or 1 based on a threshold score $S_T$, wherein the threshold score $S_T$ may be predetermined.

Thus, based on the respective input data (i.e. pixel intensity ($p_i$) per pixel of the respective images (b) and/or the respective determined sequence of differences in the pixel intensity ($\Delta p_i$) per pixel between two consecutive images ($\Delta$b) as input data alone or respectively in combination with the respective progress value $t_p$ and/or the information on antimicrobial agent and optionally the microorganism per respective well ($M_v$, $M_t$), the deep learning neural network (10) predicts microorganism growth or microorganism growth inhibition for the incubated sample microorganism.

The deep learning neural network architectures of models 1 and 2 may generally be the same in terms of layers and parameters. Preferably, models 1 and 2 use one or more suitable layers for spatio-temporal feature extraction. The extracted and preferably condensed image features are subsequently preferably concatenated together with the progress value $t_p$ and preferably the information on the antimicrobial agent and optionally the microorganism ($M_v$) using one or more classification layers. In view of the different input data (pixel intensity ($p_i$) per pixel of the respective images (b) vs. differences in the pixel intensity ($\Delta p_i$) per pixel between two consecutive images ($\Delta$b), the models 1 and 2 may generally learn different kinds of features.

Model 3 combines the two different sets of image input data provided respectively in models 1 and 2. According to model 3A (see FIGS. 2*c*), 3*c*) and 3*f*)) the different input data are extracted using separate neural networks for feature extraction, preferably wherein the different image input data is simultaneously extracted in separate neural networks. The separate neural networks for feature extraction may exhibit the same architecture as used in models 1 and 2 respectively. The condensed information of the sequence of pixel intensity ($p_i$) per pixel (b) for the two or more images of the incubated sample microorganism and the condensed information of the determined sequence of differences in the pixel intensity ($\Delta p_i$) per pixel between two consecutive images ($\Delta$b) respectively for the two or more images may then be concatenated in a further feature extraction step 102 prior to feature classification. In feature classification the combined condensed information may further be concatenated with the progress value $t_p$. According to model 3B (see FIG. 3g)), the different input data are extracted using a first block of layers (101) and are aggregated into a three-dimensional matrix, a so called "tensor" comprising or consisting of the information of the sequence of pixel intensity ($p_i$) per pixel for the two or more, preferably eight or more, more preferably 16 or more images of the incubated sample microorganism in the well (b) and a determined sequence of differences in the pixel intensity ($\Delta p_i$) per pixel between two consecutive images ($\Delta$b) respectively for the two or more, preferably eight or more, more preferably 16 or more images of the incubated sample microorganism in the well as well as the value of the time progress $t_p$ and the information on antimicrobial agent and preferably the microorganism of the respective well ($M_t$). Due to the aggregation of the input data into a three-dimensional matrix model 3B allows using a simpler CNN, which may not need to be changed in case new features may be added to the input data. $S_o$, the three-dimensional CNN model may be regarded as more robust in view of further input data changes and/or may be regarded more universal.

In view of the need of preprocessing in order to provide a sequence of differences in the pixel intensity ($\Delta p_i$) as input data ($\Delta$b), the models 2 and 3 may be slower than the model 1. The number of preprocessing operations generally grows linearly with the number of images.

In this regard, the model 1 may be beneficial for inventive methods and systems that provide limited computing power, e.g., standalone devices that constantly improve the performance of neural network using incoming data, but cannot use a centralized database, such as point of care (POC) field devices.

The inventors have furthermore found out, that performance of model 2 may be reduced in comparison to models 1 and 3. One explanation may be that the decreased performance may be due to the subtraction of pixel values of one image from another. Even though, this kind of operation distils the information about a change in time, it may also remove other information such as an increase in background brightness and initial brightness. Moreover, it may increase noisiness of the data. Nevertheless, model 2 may be beneficial for those systems that cannot provide repeatable background information, e.g., which may be caused by a poor quality of camera or by changing lighting conditions.

Model 3 uses input data that is almost two times bigger in terms of parameters than compared to models 1 and 2 due to the use of the sequence of pixel intensity ($p_i$) (b) and the sequence of differences in the pixel intensity ($\Delta p_i$) ($\Delta$b). Thus, the training time and the inference for the prediction generally may take longer for model 3 in comparison to models 1 and 2. Nevertheless, model 3 may be beneficial for inventive methods and systems that can provide suitable computing power or have access to GPU unit, as model 3 may provide the lowest false positive and false negative rates. Furthermore, model 3 generally provides an improved generalization on new data and is more robust to changing pixel intensity parameters across the machines. This advantage is presently explained in view of the fact that classic input of sequence of pixel intensity provides information about initial pixel intensity and anomalies occurring on the images, while the input of the determined sequence of differences of pixel intensities provides information about the dynamic change during the incubation process more explicitly.

As set out above, the input data may preferably also include the progress value $t_p$ used in (i), (ii) or (iii), wherein in (iii) the same progress value $t_p$ is used. According to a further preferred embodiment of the present invention, the progress value may be selected from the range $0.2 \le t_p \le 0.9$, alternatively selected from the range $0.3 \le t_p \le 0.8$, alternatively selected from the range $0.4 \le t_p \le 0.75$, or alternatively selected from the range $0.5 \le t_p \le 0.6$. For fast growing microorganisms the progress value may generally also be smaller, preferably in the range of $0.2 \le t_p \le 0.6$. For slow growing microorganisms the progress value may preferably be in the range of $0.5 \le t_p \le 0.9$.

In general, in case a lower progress value $t_p < 0.4$ may be predetermined for the inventive method, the models 1, 2 or 3 can be used for early detection of microbial growth, but may provide limited accuracy, i.e. increased false positive and false negative ratios. In case a higher progress value $t_p \ge 0.4$ may be predetermined for the inventive method, the inventive method requires a longer incubation time (i.e., an increased time period for data collecting), but the inventive method provides outputs and, thus, predictions of microbial growth or no growth with higher sensitivity and specificity. Thus, the progress value $t_p$ may be predetermined depending on the needs. As set out above, the risk of false negative predictions at lower progress values and/or false positive predictions at higher progress values can furthermore be reduced by using the progress value as additional input data.

In general, the inventive models 1 to 3 are sensitive to slightest increase in pixel intensity ($p_i$) while the progress value is low, as in early time of incubation the microorganism growth is comparatively low. Still, there exists a way for tuning the model for sensitivity or specificity by adapting the training of the deep neural network. During the training, in most of the deep learning frameworks including TensorFlow and PyTorch, the user may specify weight assigned to every image in the training dataset or to a whole class. In this manner, one of the classes may be favoured during training leading to higher sensitivity when more importance is given to a positive class or higher specificity otherwise. In a meticulous scenario, one can define the weight of every sample in training which may lead to improved performance on difficult examples, for instance the sequences in which some kind of disturbance occurred and or images of low progress.

As mentioned above, the inventive method provides an output score ($S_o$) $0 \le S_o \le 1$, wherein $S_o = 0$ represents a distinct microorganism growth inhibition and $S_o = 1$ represents a distinct microorganism growth values ranging from 0 to 1. This output score may also be used to tune the trade-off between sensitivity and specificity of the respective models 1, 2 or 3. In view of errors resulting from false negatives predictions (i.e. microbial growth despite predicted output score $S_o = 0$), the sensitivity may be tuned by, e.g., lowering the threshold score $S_T$ from 0.5 to 0.3. Such a lowering of the threshold $S_T$ may, however, generally increase model sensitivity at the cost of general model accuracy.

In general, the threshold $S_T$ can be predetermined, such as $S_T = 0.5$ or a value relating to an a priori knowledge of the incubation system. In case no a priori knowledge is available, the threshold $S_T$ may be predetermined at the lowest point of the output score distribution for different progress values providing most efficient statistical discrimination of the respective sets.

Thus, according to a preferred embodiment of the present invention, a threshold value $S_T$ of the output score $S_o$ may be predetermined as a function of the selected progress value $t_p$ and optionally as a function of sensitivity and/or specificity of the prediction, wherein in case the output score $S_o$ exceeds the predetermined threshold $S_T$ for the selected progress value $t_p$, the signal prediction is classified 1 representing a distinct probability of microorganism growth, or wherein in case the output score $S_o$ is below a predetermined threshold $S_T$ for the selected progress value $t_p$, the signal prediction is classified 0 representing a distinct probability of microorganism growth inhibition.

According to an additional or alternative preferred embodiment of the present invention, the imaging device in step b) of the inventive method may be selected from a digital camera, preferably a digital camera enabling single channel pixel intensity or multiple channel pixel intensity. Preferably, the digital camera shall enable taking images having a single-channel with 8-bit depth. More preferably, the image may exhibit 24×24 pixels. Suitable images of pixel intensities are shown in FIGS. 4*a*), 4*b*), 5*a*) and 6*a*).

According to an additional or alternative preferred embodiment of the present invention, the deep learning neural network of step c) of the inventive method may comprise one or more recurrent layers, such as convolutional Long Short-Term Memory (ConvLSTM) layers. ConvLSTM are beneficial for spatio-temporal feature extraction (see FIGS. 5*b*) and 6*b*)), as ConvLSTM not only establishes a timing relationship like in LSTM, but also extracts local spatial characteristics (see Xingjian Shi et al. "Convolutional LSTM Network: A Machine Learning Approach for Precipitation Nowcasting". In: arXiv:1506.04214 [cs] (September 2015). arXiv: 1506.04214 version: 2). Thus, recurrent layers, in particular ConvLSTM2D layers, seem to be a preferred choice for spatio-temporal feature extraction. According to an additive or alternative preferred embodiment of the present invention, two or more alternating recurrent layers and Pooling layers and optionally two or more respectively alternating recurrent layers, Pooling layers and BatchNormalization layers are used in sequential order to extract spatio-temporal features of the images. The use of pooling layers is beneficial in order to decrease the size of the sequences in spatial as well as in temporal dimension to obtain smaller models. The inventors found out that even the use of two pooling layers may ensure to accurately distinct between positive and negative signals.

According to a further additive or alternative preferred embodiment of the present invention, the spatio-temporal feature extraction of the deep learning neural network in step c), preferably in step ciii) of the inventive method is followed by feature transformation using one or more Dense layers and optionally one or more respectively alternating Flatten layers, BatchNormalization layers and Dropout layers. The use of dense layer may facilitate the concatenation of the condensed information of the sequence of pixel intensity ($p_i$) and/or sequence of differences in the pixel intensity ($\Delta p_i$) (see FIGS. 5*b*) and 6*b*)) and the progress value $t_p$. For the purpose of better generalization of the models the inventive method may use one or more batch normalization layers and/or dropout layers. This inventive embodiment may improve the model performance for new data, i.e. data provided by a different system than the training data.

According to model 3B, the inventive embodiments of the convolutional neural network do not use recurrent layers anymore. Instead, the first block of layers (101) into which the input data is fed comprises or consists of a convolutional layer, a batch normalization layer and a ReLU activation layer, preferably in this order. The feature extractor 102 comprises or consists of one block or two, three, four, five or more blocks in series, preferably five blocks in series respectively comprising or consisting of a convolutional layer (*), a batch normalization layer, a ReLU activation function layer, a further convolutional layer, a further batch normalization layer (**), a layer summing the input to the convolutional layer (*) and the output of the further batch normalization layer (), and another ReLU activation function layer, preferably in this order. The last block of layers 103** preferably comprises or consists of a convolutional layer, a batch normalization layer, a ReLU activation function layer, a fully connected (dense) layer, and a sigmoid activation layer, preferably in this order.

According to a further additive or alternative preferred embodiment of the present invention, the deep learning neural network used in step c) of the inventive method or in feature c) of the inventive system was previously trained

- with a separate models approach comprising two or more models, wherein each model is respectively trained with sequences of two or more, preferably eight or more, more preferably 16 or more images of a sample of incubated microorganism for a respective progress value selected from the range $0 \leq t_p \leq 1$ as input data, wherein the images respectively provide information on the pixel intensity ($p_i$) per pixel and are respectively binary labelled with 0 representing microorganism growth or 1 representing microorganism growth inhibition and wherein the images are consecutively, preferably evenly, distributed within the respective progress value $t_p$, or
- with a one model approach, wherein in each training epoch the same model is trained with a respective sequence of two or more, preferably eight or more, preferably 16 or more images of a sample of incubated microorganism as input data, wherein the images respectively provide information on the pixel intensity ($p_i$) per pixel and are respectively binary labelled with 0 representing microorganism growth or 1 representing microorganism growth inhibition and wherein the images are consecutively distributed for a respective randomly selected progress value $t_p$, wherein the random selection of the progress value $t_p$ is preferably conducted from a set of {0.2, 0.3, 0.4, 0.5, 0.6, 0.75, 0.8, 0.9, 1.0} or from a continuous distribution in the range of $0.2 \leq t_p \leq 1.0$, wherein the one model approach optionally comprises the selected progress value $t_p$ as further input data.

In the separate models approach n different neural networks (NN) models are thus created to inference results in n various points in time of the incubation time of the analysis. The one model approach in contrast, presupposes usage of one universal neural network model at any time during the analysis. The two proposed model approaches differ significantly when it comes to inference state, but also in training procedure they are described in more depth in the following.

The separate models approach is based on the finding that separate models trained on different sub-sequences of the whole images sequences will act better for a particular analyzing time frame. This finding is presently explained by the increasing number of models that directly increase computational capacity of the whole system comprising the set of different n models. Therefore, the inventive method and system may be more likely to distinguish possible microbial growth behaviours that are related directly to the specific time during the analyzing time frame.

With respect to the training of the separate models approach a first model architecture is preferably trained with the labelled sequence of images of progress value $t_p=1$ and the subsequent models are trained with labelled sequences of images for respectively decreasing progress values $t_p<1$. In order to provide an inventive method and system, which is a collection of separate models, it is preferred to save every best model (in terms of validation accuracy) from the training for a particular progress value $t_p$. For method validation purposes models may be trained with progress values $t_p$ selected from 0.2, 0.4, 0.6, 0.8, 1.

In the inference stage, i.e. during machine operation, only one of the set of n models is making predictions for the specific progress value $t_p$ of incubation, i.e. the specific analyzing time period.

The inventors found out that the one model approach generally seems to be more universal and less error prone, which is presently explained in view of the fact that only one model is trained with all the information. However, it also seems presumably less capable to learn all the different behaviours of microbial growth due to much more restricted parameter space in comparison to the collection of separate k models from the previous approach. According to an additive or alternative preferred embodiment, the one model approach is fed furthermore with the progress value $t_p$ in order to enable the model to autonomously calibrate sensitivity for a particular analyzing time frame.

The inventors have furthermore found out that for certain microorganisms and G or antimicrobials used in the incubated sample in the well, the inventive one model approach method works better or worse than others.

In the following we provide a list of examples of antimicrobial agent/microorganism pairs for which the inventive one model approach solution worked in an excellent way (accuracy, sensitivity and specificity were 100%):

| Antimicrobial/antibiotic | Microbial/Bacteria |
|---|---|
| Tigecycline | *Staphylococcus* |
| Ciprofloxacin | *Enterococcus* |
| Cefoxitin | *Staphylococcus* |
| Rifampicin | *Staphylococcus* |
| Linezolid | *Enterococcus* |
| Gentamicin | *Staphylococcus* |
| Moxifloxacin | *Enterococcus* |
| Ticarcillin-clavulanic acid | *Enterobacterales* |
| Ticarcillin-clavulanic acid | *Enterococcus* |
| Amoxicillin | *Enterobacterales* |

In the following, the inventors found that for the following list of pairs the inventive one model solution worked not as good:

| Antimicrobial/antibiotic | Microbial/Bacteria |
|---|---|
| Minocycline | *Acinetobacter* |
| Meropenem | *Acinetobacter* |
| Tetracycline | *Acinetobacter* |
| Cefalexin | *Enterobacterales* |
| Amoxicillin-clavulanic acid | *Enterobacterales* |

According to a further additive or alternative preferred embodiment of the one model approach, the present invention provides a solution for resolving this problem by using information on the antimicrobial agent used in the respective well and optionally information on the microorganism contained in the sample of the respective well as further input data. Providing a vector or matrix of both microorganism under test and antimicrobial under test is preferably used when testing the antimicrobial resistance. In case the type of microorganism is tested, the microorganism is usually unknown at time of testing and, thus, the vector regarding the microorganism may not be used as input data. The inventors found that in particular for the information of the following pairs of antibiotics and bacteria as input data according to all aspects and embodiments of the present invention, the results are improved with respect to accuracy, sensitivity and/or specificity:

| Antimicrobial/antibiotic | Microbial/Bacteria |
|---|---|
| Minocycline | *Acinetobacter* |
| Piperacillin-tazobactam | *Acinetobacter* |
| Meropenem | *Acinetobacter* |
| Cefalexin | *Enterobacterales* |
| Imipenem | *Enterobacterales* |
| Nitrofurantoin | *Enterobacterales* |
| Trimethoprim-sulfamethoxazole | *Staphylococcus* |
| Ceftazidime | *Staphylococcus* |
| Imipenem | *Pseudomonas* |
| Cefepime | *Pseudomonas* |
| Vancomycin | *Enterococcus* |

Training in one model approach generally runs in different manner, because only one model is trained during the whole training process. Accordingly, in every epoch the progress value $t_p$ may be randomly selected for every record from the dataset. Random selection of the progress value $t_p$ may preferably conducted in two variances:

from a set {0.2, 0.4, 0.6, 0.8, 1.0} or from a continuous uniform distribution from 0.2 to 1.0 inclusively.

Thus, in every epoch the one model is trained with a completely different combination of sub-sequences of images from the original dataset of records, which serves as data augmentation and leads to better generalization by the model. As already mentioned above, the one model approach may also be fed with the progress value $t_p$ as a second input and concatenated with condensed information of the image sequence. However, the one model approach may also be trained without a separate input of the progress value $t_p$ to the one model approach. In addition, information on the antimicrobial agent used in the respective well and optionally information on the microorganism contained in the sample of the respective well may also be used as further input data in vector format $M_v$ or in matrix format $M_t$ as set out hereinbefore.

The inference of the one model approach is generally straightforward, because only one model is used in this approach. Therefore, for prediction only sequence of images and optionally the progress variable as well as the information on the antimicrobial agent used in a respective well and/or the microorganism to be tested in a respective well is needed in any moment of the inventive method.

In summary, the above mentioned different model approaches lead to five different approaches, namely the separate models approach (in case five progress values $t_p$ are used five models approach)

the one model approach, wherein the one model approach may be used i. with additional discrete progress value $t_p$ input, ii. with additional continuous progress value $t_p$ input, iii. without direct additional progress value $t_p$ input, but wherein the images used for training resulted from a discrete progress, and iv. without direct additional progress value $t_p$ input, but wherein the images used for training resulted from a continuous progress.

In addition, any of the separate models or one model approaches as set out above can be used with or without the information on the antimicrobial agent used in the respective well and with or without information on the microorganism contained in the sample of the respective well.

In general, the separate models approach or the one model approach is respectively optimized with respect to the density of the output score $S_o$ for the binary values 0 and 1. Any suitable optimizer may be used, such as Stochastic Gradient Descent (SGD) or ADAM algorithm optimizer, wherein ADAM algorithm as optimizer is preferred in view of proven experimentally convergence in a broad range of problems. More preferably, the optimization includes using a loss function, preferably in basic fit( ) loop with binary cross-entropy as a loss function as follows:

$$H_p(q) = -\frac{1}{N}\sum_{i=1}^{N} y_i \cdot \log(p(y_i)) + (1 - y_i) \cdot \log(1 - p(y_i))$$

wherein:

q represents a set,

N represents a number of samples in the set q, $y_i$ represents a label for a given sequence (0 or 1), $p(y_i)$ represents a prediction for a given sequence (continuous value between 0 and 1).

Minimizing the mentioned cost function derived from information theory, which is the entropy of the random variable $y_i$ (with a slight modification), can be interpreted as the desire to obtain a situation in which the output score values $S_o$ will be exactly 0 or 1 for the appropriate classes of signals. Then the function will assume a global minimum equal to 0. However, in practice the output score value $S_o$ is received of a random variable in the continuous range from 0 to 1, the density of which has higher values near 0 and 1.

According to the present invention the antimicrobial susceptibility of any suitable microorganism can be tested. Preferably the microorganism is selected from the list consisting of bacterium, e.g. aerobic or anaerobic bacterium including *mycobacterium*, and fungus. According to one embodiment of the present invention, the microorganism is selected from the group consisting of bacterium including aerobic bacterium or anaerobic bacterium.

With respect to the first inventive aspect, the microorganism inoculum and suitable broth dilutions for the respective microorganism may be prepared according to standard methods in the art, in particular as described by EUCAST (The European Committee on Antimicrobial Susceptibility Testing; http://www.eucast.org) and CLSI (Performance Standards for Antimicrobial Susceptibility Testing, 22th Edition; CLSI document M100-S22. Wayne, P A: Clinical and Laboratory Standard Institute; 2012). The respective described standard methods for antimicrobial susceptibility testing for bacteria, mycobacteria and fungus are incorporated herein with reference. According to the present invention the microorganism inoculum, which is usually an overnight culture, or a portion of an overnight culture, of a tested microorganism is diluted in a suitable growth medium, such as the liquid broth dilution (synonymously also referred to as "medium suitable for broth dilution AST"). A sample of this diluted inoculum (synonymously also referred to as "a sample of the medium containing the diluted inoculum", "a sample of broth dilution of a microorganism inoculum" or "a sample of a microorganism inoculum diluted in a growth medium") is then used in step a) of the inventive method. In particular when testing bacteria as microorganisms, the broth may be selected from un-supplemented cation-adjusted Mueller-Hinton broth (MH broth), which is used for testing of non-fastidious organisms according to the ISO standard 20776-1, 2006, or cation-adjusted MH broth supplemented with 5% lysed horse blood and 20 mg/L β-NAD (MH-F broth), which is used for testing *Streptococcus* spp. (including *S. pneumoniae*), *Haemophilus influenzae, Moraxella catarrhalis, Listeria monocytogenes, Campylobacter jejuni* and *coli, Pasteurella multocida, Corynebacterium* spp., *Aerococcus sanguinicola* and *urinae, Kingella kingae* and several other fastidious organisms. Un-supplemented MH broth may also be purchased from commercial sources.

According to a further additive or alternative preferred embodiment of the present invention, the inventive method and system may be used for simultaneously predicting the microbial growth or no-growth for two or more samples. The samples may relate to the same or of different microorganisms. The samples are respectively separately incubated with the incubating device. In this case, the inventive method may provide in step b) that each image of the sequence of images respectively comprises the plurality of images of the separately incubated two or more sample microorganisms of step a). In this case, each digital image comprising the plurality of images of separate samples is respectively transformed to form a matrix providing separate images (crops) for the respective two or more sample microorganisms as input data for the deep learning neural network in step c) of the inventive method.

The image transformation may be conducted by transforming the image into a grid of a plurality of (mini) images/crops of the separate incubated samples respectively. In this regard, one or more reference points may be detected on the taken image. In this regard, contours on a specified channel may be detected and ratios of distances between reference points may be calculated to verify correctness of detected points. A default grid may be loaded in correlation to the one or more reference points. The perspective transform of the images may then be calculated (forming a matrix), e.g. using two sets of four reference points. Preferably, followed by processing the taken image with obtained perspective transform. The mini images/crops of respective time points of incubation of the separate incubated samples may then be horizontally stacked forming a sequence of images of the respective incubated samples (see each line in FIGS. 4*a*) and 4*b*). Each of the mini images of the respective incubated sample (e.g. of each of the microchambers of a microtiter plate respectively) may exhibit 24×24 pixels.

The inventively used incubating device may be any suitable incubating carrier (alternatively called carrier) comprising one or more compartments suitable for AST, wherein the or at least part of the compartments comprise respectively a single antimicrobial agent or a combination of antimicrobial agents. The incubating carrier also generally facilitates image taking of the one or more incubated sample microorganism inoculum in step b) of the inventive method as well as avoidance of cross contamination between test assays. Such an incubation carrier may be selected from the group consisting of microtiter plate, tube, e.g. Eppendorf tube, petri dish or microfluidic chip. The incubation carrier represents preferably a microtiter plate or a microfluidic chip, as multiple test assays can be incubated simultaneously. A microfluidic chip may be still preferred as carrier according to all inventive aspects, as it may house equal to or greater than 100 incubation compartments, preferably equal to or greater than 128 incubation compartments, more preferably equal to or greater than 320 incubation compartments, even more preferably equal to or greater than 640 incubation compartments, and more preferably equal to or greater than 1280 incubation compartments. The (incubation) compartment of a microfluidic chip may synonymously also be referred to as incubation segment or incubation well or incubation chamber. The incubation carrier to be preferably used for the present invention may also comprise means for facilitating incubation, such as temperature adjusting means and/or means for exchange of gases. Very preferred microfluidic chips suitable for the present invention are described in particular in international patent applications WO 2019/185927 A1 and WO 2019/185885 A1 (both in the name of Bacteromic sp. z.o.o., also the present applicant) and the content concerning the microfluidic chip of both applications WO 2019/185927 A1 and WO 2019/185885 A1 are incorporated herein by reference.

The one or more compartments of the incubation carrier may respectively comprise a single antimicrobial agent or a combination of two, three, four or more antimicrobial agents and optionally further excipients as necessary. The antimicrobial agent (synonymously also referred to as "antimicrobial") or combination of antimicrobial agents may be selected from the group of agents inhibiting the growth of bacteria, mycobacteria, and/or fungi. In particular, the antimicrobial agent or the combination of antimicrobial agents may comprise a bacteriostatic agent, a bactericide agent, a fungistatic agent or a fungicide agent. The single antimicrobial agent or the combination of antimicrobial agents and optionally the further excipients are dispensed into the respective compartments of the carrier by suitable means, wherein the final concentration of the antimicrobial agent(s) in the respective compartment must be known or determinable. In particular, in case a microtiter plate or a microfluidic chip is used, the single antimicrobial agent or the combination of two or more antimicrobial agents and optional further excipients are e.g. spotted into the respective compartments (wells of the microtiter plate or incubation compartments/segments/wells of a microfluidic chip). In case the antimicrobial agent is admixed with the inoculated microorganism in the dilution ration 1:1, then the concentration of the antimicrobial agent in the respective compartment must be twice as high as the target concentration. For example, equal portions (i.e., 100 μl or 50 μl) of the inoculated broth dilution and the antimicrobial agent dilution are admixed in a well of a multitier plate (e.g., Corning® 96 Well CellBIND® Microplate, https://www.sigmaaldrich.com/catalog/product/sigma/cls3340, Corning™ Costar™ Flat Bottom Cell Culture Plates, https://www.fishersci.cor/shop/products/costar-cell-culture-plates-17/0720090) that allows for the measurement of optical properties of the sample. Preferably 3 repetitions for each test assay are prepared. When using other mixing ratios, then the respective antimicrobial agent concentration needs to be used. In case a quantitative determination of antimicrobial susceptibility, in particular the minimum inhibitory concentration shall be determined with the present invention, two or more compartments of the carrier comprise different concentrations of the single antimicrobial agent or the combination of antimicrobials. Preferably, the series of different concentrations is used in accordance with the standards provided by EUCAST (The European Committee on Antimicrobial Susceptibility Testing; http://wwweucast.org.) and CLSI (Performance Standards for Antimicrobial Susceptibility Testing, 22$^{th}$ Edition; CLSI document M100-S22. Wayne, P A: Clinical and Laboratory Standard Institute; 2012).

As set out above, the information on the antimicrobial agent used in a respective well may be used as further input data for the first inventive embodiment. The information on antimicrobial agent and microorganism of a well may respectively either be provided in form of a vector having the format n+1 or alternatively in form of a matrix, wherein each of the n+1 fields of the vector is a matrix, preferably a 24×24 matrix, and in case the antimicrobial agent is present in the well, the matrix is full of ones.

According to another additive or alternative preferred embodiment, the inventive method may use 2, 10, 20, 30, 40, 50, 60 or more incubation devices for essential parallel inventive prediction of microorganism growth or no-growth. In the context of the present invention, "parallel inventive prediction of microorganism growth or no-growth" means that the plurality of incubation devices are sequentially imaged as set out before. In other words, one incubation carrier comprising one or more, preferably more incubation chambers, is imaged at a time and subsequently the next incubation carrier comprising one or more, preferably more incubation chambers, is imaged.

The aforementioned (preferred) embodiments of the first aspect of the present invention may be combined throughout. In particular, the different preferred embodiments of the first aspect of the present invention can alternatively or in addition be combined with each other.

All aforementioned embodiments including the combination of preferred embodiments in relation to the first aspect of the present invention can also be used for combination with (preferred) embodiments of the second and third aspect of the present invention.

The second aspect of the present invention relates to a rapid antimicrobial susceptibility testing system for predicting microorganism growth or microorganism growth inhibition of a microorganism inoculum in a phenotypic antimicrobial susceptibility test (AST), the system comprising or consisting of:

a) an incubation assembly configured for housing an incubation device for incubating a sample of a microorganism with a single antimicrobial agent or a combination of antimicrobial agents, b) an imaging device configured to taking a sequence of two or more, preferably eight or more, more preferably 16 or more digital images of the incubated sample microorganism of feature a) on the incubating device, wherein the imaging device is configured to provide information on pixel intensity ($p_i$) per pixel for each image and wherein the imaging device is further configured to taking the sequence of images consecutively distributed within a progress value ($t_p$) with $0<t_p<1$, wherein the progress value $t_p$ represents a ratio of a proportional incubation time period for the consecutively distributed sequence of images of the incubated sample microorganism divided by an overall incubation time period from start to end of the incubation for the respective microorganism, and c) a computer assembly comprising one or more processors, and an analysis module comprising a deep neural network unit configured to extract spatio-temporal features of the sequence of images and to classify the respective images and one or more computer-readable media storing instructions that, when executed by the one or more processors, cause the one or more processors to perform predicting microorganism growth or microorganism growth inhibition for the incubated sample microorganism as a function of an output score ($S_o$) $0 \leq S_o \leq 1$ of the deep learning neural network, wherein $S_o=0$ represents a distinct microorganism growth inhibition and $S_o=1$ represents a distinct microorganism growth, and wherein the deep learning neural network is configured to use as input data (i) a sequence of pixel intensity ($p_i$) per pixel for the two or more, preferably eight or more, more preferably 16 or more images of feature b), or (ii) a determined sequence of differences in the pixel intensity ($\Delta p_i$) per pixel between two consecutive images respectively for the two or more, preferably eight or more, more preferably 16 or more images of feature b), or (iii) a sequence of pixel intensity ($p_i$) per pixel for the two or more, preferably eight or more, more preferably 16 or more images of the incubated sample microorganism of feature b) and a determined sequence differences in the pixel intensity ($\Delta p_i$) per pixel between two consecutive images respectively for the two or more, preferably eight or more, more preferably 16 or more images of feature b).

Preferably, the deep learning network of the inventive rapid antimicrobial susceptibility testing system is further configured to additionally use as input data (iv) the respective progress value $t_p$ used in feature (i), (ii) or (iii), wherein in (iii) the same progress value $t_p$, and/or (v) information on the antimicrobial agent present in the incubated sample in step a) and/or (vi) information on the microorganism present in the incubated sample in step a).

According to an additive or alternatively preferred embodiment of the inventive rapid antimicrobial susceptibility testing system for predicting microorganism growth or microorganism growth inhibition, the incubation assembly is configured for housing one or more incubation devices and wherein preferably each incubation device is respectively configured for incubating two or more sample microorganisms.

Suitable incubating devices are described in detailed with respect to the first inventive aspect. These incubating devices, in particular incubating carriers may also be used in any combination with respect to the second inventive aspect.

Furthermore, suitable imaging devices are described with respect to the first inventive aspect. These imaging devices, preferably digital cameras, more preferably digital cameras providing low resolution information, i.e. spatial resolution in the range of 0.1 to 0.01 mm/pixel more preferably 0.075 mm/pixel or 0.05 mm/pixel, may also be used in any combination with respect to the second inventive aspect.

According to an additive or alternatively preferred embodiment of the inventive rapid antimicrobial susceptibility testing system for predicting microorganism growth or microorganism growth inhibition, the imaging device may be configured to taking an image of the respective incubating devices at a time, wherein each image of the sequence of images respectively comprises a plurality images of the separately incubated two or more sample microorganisms. The analysis module is in this case preferably configured to preprocess the images by respectively transforming each digital image to form a matrix providing separate (mini) images/crops for the respective two or more separate samples as input data for the deep learning neural network in feature c).

This embodiment relates in other words to the quasi simultaneous assessment of multiple inoculated microorganism samples. As already described with respect to the first inventive aspect, this embodiment may use a suitable incubation device, such as incubation carrier. In particular, wherein the incubation carriers may provide 2, 10, 50, 100, 200, 300, 400, 500, 600, 640 or more separated areas, preferably microchambers, for isolated incubation of the respective 2, 10, 50, 100, 200, 300, 400, 500, 600, 640 or more inoculated samples of feature a). Furthermore, the inventive system may use 2, 5, 10, 20, 30, 40, 50, 60 or more incubating devices in parallel for conducting the inventive method of the first aspect. In other words, the plurality of incubation devices, preferably incubation carriers is sequentially images and, thus, processed.

According to the present invention, the analysis model including the deep learning neural network may be implemented on board of the inventive rapid antimicrobial susceptibility testing system for predicting microorganism growth or microorganism growth inhibition of a microorganism inoculum in a phenotypic antimicrobial susceptibility test (AST). Alternatively, the analysis model including the deep learning neural network may be implemented on a separate computing system, such as a computer server or computer cloud system, which is direct or indirect computing communication with the inventive rapid antimicrobial susceptibility testing system for predicting microorganism growth or microorganism growth inhibition of a microorganism inoculum in a phenotypic antimicrobial susceptibility test (AST).

The aforementioned (preferred) embodiments of the second aspect of the present invention may be combined throughout. In particular the different preferred embodiments of the second aspect of the present invention can alternatively or in addition be combined with each other.

All aforementioned embodiments including the combination of preferred embodiments in relation to the second aspect of the present invention can also be used for combination with (preferred) embodiments of the first or third aspect of the present invention.

The third aspect of the present invention relates to a use of a deep neural network unit configured to extract spatiotemporal features of a sequence of two or more images of an incubated sample of microorganism and to classify the respective images for predicting microorganism growth or microorganism growth inhibition of the incubated sample microorganism as a function of an output score ($S_o$) $0 \leq S_o \leq 1$ of the deep learning neural network, wherein $S_o=0$ represents a distinct microorganism growth inhibition and $S_o=1$ represents a distinct microorganism growth, characterized in that the sequence of images is consecutively distributed within a progress value ($t_p$) with $0<t_p<1$, wherein the progress value $t_p$ represents a ratio of a proportional incubation time period for the consecutively distributed sequence of images of the incubated sample microorganism divided by an overall incubation time period from start to end of the incubation for the respective microorganism, and wherein the deep learning neural network is configured to use as input data (i) a sequence of pixel intensity ($p_i$) per pixel for the two or more, preferably eight or more, more preferably 16 or more images of the incubated sample microorganism of feature b), or (ii) a determined sequence of differences in the pixel intensity ($\Delta p_i$) per pixel between two consecutive images respectively for the two or more, preferably eight or more, more preferably 16 or more images of feature b), or (iii) the sequence of pixel intensity ($p_i$) per pixel for the two or more, preferably eight or more, more preferably 16 or more images of the incubated sample microorganism of feature b) and a determined sequence of differences in the pixel intensity ($\Delta p_i$) per pixel between two consecutive images respectively for the two or more, preferably eight or more, more preferably 16 or more images of feature b).

Preferably, the deep learning network further uses as input data (iv) the respective progress value $t_p$ used in feature (i), (ii) or (iii), wherein in (iii) the same progress value $t_p$, and/or (v) information on the antimicrobial agent present in the incubated sample in step a) and/or (vi) information on the microorganism present in the incubated sample in step a).

Thus, according to an additive or alternative preferred embodiment, the input data may also contain information on the antimicrobial agent used in a respective well and optionally the microorganism of the sample present in the respective well.

This additional input data may be used in form of a vector information ($M_v$) on the antimicrobial agent used in a respective well and optionally a vector ($M_v$) containing information on the microorganism of the sample present in the respective well. The respective vectors may be built as follows. If there are n antimicrobial agents considered, the vector for antimicrobial agents has n+1 fields. Each field represents a single antimicrobial agent and the last field represents the information "no antimicrobial agent present in the well". For each well, only one of the vector fields exhibits the value 1, representing the respective antimicrobial agent type or "no antimicrobial agent present in the well", whereas the remaining vector fields exhibit the value 0. In analogous way, the vector containing information on the microorganism of the sample is built. Accordingly, if there are n microorganisms considered, the vector for microorganism in the sample has n+1 fields. Each field represents a single microorganism and the last field represents the information "no microorganism present in the well". For each well, only one of the vector fields exhibits the value 1, representing the respective microorganism type or "no microorganism present in the well", whereas the remaining vector fields exhibit the value 0.

According to one embodiment of the present invention, the respective vector information ($M_v$) is concatenated in later layers of the deep learning neural network with the already condensed information of the pixel intensities, preferably in the layer(s) connected to the classification layers (fully connected layers), so that it can exhibit more weight for adapting the classification (see FIGS. 3*d*) to 3*f*)).

According to an alternative embodiment of the present invention, the progress value $t_p$ and the information on antimicrobial agent and preferably the microorganism of a respective well is concatenated in an earlier block of layers, such as block 101, of the deep learning neural network (see FIG. 3*g*)). The input data is preferably aggregated into a three-dimensional matrix, in particular a "tensor", wherein this tensor (also "single data sample") comprises or consists of the information of the sequence of pixel intensity ($p_i$) per pixel for the two or more, preferably eight or more, more preferably 16 or more images of the incubated sample microorganism in the well (b) and a determined sequence of differences in the pixel intensity ($\Delta p_i$) per pixel between two consecutive images ($\Delta$b) respectively for the two or more, preferably eight or more, more preferably 16 or more images of the incubated sample microorganism in the well as well as the value of the time progress $t_p$ and the information on antimicrobial agent and preferably the microorganism of the respective well respectively in form of a matrix ($M_t$), wherein each of the n+1 fields of the vector is a matrix, preferably a 24×24 matrix, and in case the antimicrobial agent is present in the well, the matrix is full of ones. In case of using 72 antimicrobial agents and 12 bacteria types as microorganisms tested in a well using a 24×24 matrix, a single input sample is a tensor in three-dimensional form of size 117×24×24. Due to the change of the vector size n+1 of the information on antimicrobial agent and preferably the microorganism of the respective well into a three-dimensional matrix format ($M_t$) without addition of any further information, the provided information in a single data sample may be in part redundant. Nevertheless, the use of input data having a three-dimensional matrix allows using a simpler CNN, which may not need to be changed in case new features may be added to the input data. So, the three-dimensional CNN model may be regarded as more robust in view of further input data changes and/or may be regarded more universal.

The use of the information on the antimicrobial agent used in the respective well and optionally the microorganism present in the respective well may also reduce the risk of false negative predictions (prediction of microorganism growth inhibition), such as when using slow growing microorganisms, or false positive predictions (prediction of microorganism growth), in particular when using fast growing microorganisms.

In this regard, we refer to your argumentation set out above.

According to an alternative or additive preferred embodiment, the deep learning neural network was previously trained with a separate models approach comprising two or more models, wherein each model is respectively trained with sequences of two or more, preferably eight or more, more preferably 16 or more images of a sample of incubated microorganism for a respective progress value selected from the range $0 \leq t_p \leq 1$ as input data, wherein the images respectively provide information on the pixel intensity ($p_i$) per pixel and are respectively binary labelled with 0 representing microorganism growth or 1 representing microorganism growth inhibition and wherein the images are consecutively, preferably evenly distributed within the respective progress value $t_p$, preferably wherein the first model is trained with the labelled sequence of images of progress value $t_p=1$ and the subsequent models are trained with labelled sequences of images for respectively decreasing progress values $t_p<1$, or with a one model approach, wherein in each training epoch the same model is trained with a respective sequence of two or more, preferably two or more, preferably 16 or more images of a sample of incubated microorganism as input data, wherein the images respectively provide information on the pixel intensity ($p_i$) per pixel and are respectively binary labelled with 0 representing microorganism growth or 1 representing microorganism growth inhibition and wherein the images are consecutively distributed for a respective randomly selected progress value $t_p$, wherein the random selection of the progress value $t_p$ is preferably conducted from a set of {0.2, 0.3, 0.4, 0.5, 0.6, 0.75, 0.8, 0.9, 1.0} or from a continuous distribution in the range of $0.2 \leq t_p \leq 1.0$, wherein the one model approach optionally comprises the selected progress value $t_p$ as further input data.

All aforementioned embodiments including the combination of preferred embodiments in relation to the first and second aspect of the present invention can also be used for combination with (preferred) embodiments of the third aspect of the present invention.

Examples

Further characteristics and advantages of the present invention will ensue from the following description of example embodiments of the inventive aspects with reference to the accompanying drawings.

All of the features disclosed hereinafter with respect to the example embodiments and/or the accompanying figures can alone or in any sub-combination be combined with features of the aspects of the present invention including features of preferred embodiments thereof, provided the resulting feature combination is reasonable to a person skilled in the art.

Deep Learning Neural Model

Deep learning neural models used in the inventive method may comprise ConvLSTM2D and MaxPooling3D layers to extract spatio-temporal features. They are followed by basic Flatten and then Dense layers to further transform signal for convenient classification. For regularization and better generalization effect we include several BatchNormalization and Dropout layers.

The layers of the deep learning model may sequentially comprise a recurrent layer, preferably ConvLSTM2D layer, to extract spatio-temporal features, a BatchNormalization layer for better generalization effect, a MaxPooling layer, preferably a MaxPooling 3D layer, to further extract spatio-temporal features. This layer arrangement/architecture may be followed by second layer architecture comprising a recurrent layer, preferably ConvLSTM2D layer, to extract spatio-temporal features, a BatchNormalization layer for better generalization effect, a MaxPooling layer, preferably a MaxPooling 3D layer, to further extract spatio-temporal features. In other words, a combination of two times a recurrent, preferably a ConvLSTM2D and subsequent MaxPooling layer architecture may provide a suitable prediction of microorganism growth and microorganism growth inhibition of a sequence of images taken with respect to a sample microorganism.

Following the feature extraction, the layer architecture may comprise a Flatten layer followed by a Dense layer in order to transform signal for convenient classification. A BatchNormalization and Dropout layer may follow for improved regularization and improved generalization. A further Dense layer may subsequently be arranged, followed by a BatchNormalization and Dense layer architecture in this order. The resulting fully connected layer may represent a Dense layer, preferably with sigmoid activation.

According to an alternative embodiment of the one-model approach (model 3B) shown in FIG. 3*g*) a first feature extractor (101) is provided into which input data relating to the respective sequence in pixel intensity ($p_i$) per pixel of the respective two or more images (b) and the respective determined sequence of differences in the pixel intensity ($\Delta p_i$) per pixel between two consecutive images as input data ($\Delta$b), the respective progress value $t_p$ as well as the respective information of antimicrobial agent and optionally information on microorganism in the respective well preferably in the three-dimensional matrix format ($M_t$) is fed and aggregated into a three-dimensional format. The architecture of the convolutional neural network (CNN) preferably does not consist of recurrent layers, such as "ConvLSTM2D" layers. Instead, the first block of layers (101) into which the input data is fed comprises or consists of a convolutional layer, a batch normalization layer and a ReLU activation layer, preferably in this order. The feature extractor 102 comprises or consists of one block or two, three, four, five or more blocks in series, preferably five blocks in series respectively comprising or consisting of a convolutional layer (*), a batch normalization layer, a ReLU activation function layer, a further convolutional layer, a further batch normalization layer (**), a layer summing the input to the convolutional layer (*) and the output of the further batch normalization layer (), and another ReLU activation function layer, preferably in this order. The last block of layers 103** preferably comprises or consists of a convolutional layer, a batch normalization layer, a ReLU activation function layer, a fully connected (dense) layer, and a sigmoid activation layer, preferably in this order.

The input data to the deep learning neural network (synonym "model") used for the inventive method and system relates to sequence of two or more images of a sample microorganism for a time period defined by the respective progress value $t_p$. As additional input data, the progress value $t_p$ and/or the respective information of antimicrobial agent and optionally information on microorganism in the respective well either in vector format n+1 ($M_v$) or in the three-dimensional matrix format ($M_t$), wherein each of the n+1 fields comprises a matrix may be used.

With respect to the training phase, the input data is generally presented to the model in the form of a tensor with dimensions (None, k, 24, 24, 1), wherein the first dimension "None" may represent the batch size, which is the smallest number of sequences on the basis of which new weights are calculated during the training. The second dimension may relate to the time dimension, which preferably defines subsequent images of the sequence in the form of a 24×24 matrix. The last dimension may represent the number of the image/photo channel—for black and white it is 1 (for a colour images/photo it would be 3—RGB).

The deep learning neural network to be used for the inventive method provides an output score correlating to the prediction of microorganism growth or microorganism growth inhibition in the form of single scalar/value in range from 0 to 1, where 0 represents lack of microorganism (preferably bacteria) growth and 1 represents distinct microorganism (preferably bacteria) growth inhibition. In other words, the output single scalar represents a conditional probability p(y|x) that may be interpreted as probability of microorganism growth as an condition of observed sequence of images within a respective proportional part of the whole incubation period.

Figure 7:
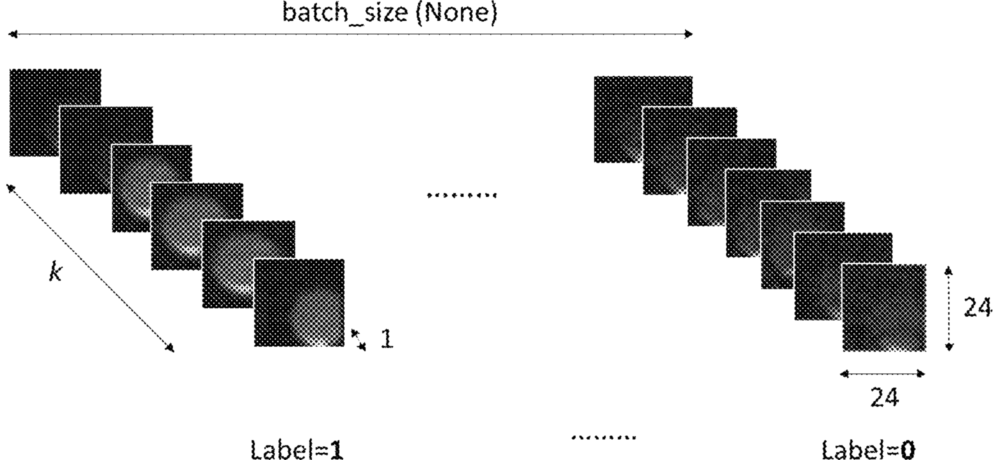
FIG. 7 represents schematic input and output data of the deep learning neural network model during training phase.

FIG. 7 represents a simplified deep learning neural network model regarding input data (batch size (None), respective k consecutive images, preferably two or more, five or more, eight or more, 16 or more, or 24 images forming a respective sequence of images for the respective progress value $t_p$, and the label 1 for microorganism growth vs. 0 for microorganism growth inhibition) and output data during training phase.

The deep learning neural network model may preferably be optimized during training. Preferably the model is optimized in basic fit( ) loop using binary cross-entropy as a loss function and ADAM algorithm as an optimizer as follows:

$$H_p(q) = -\frac{1}{N}\sum_{i=1}^{N} y_i \cdot \log(p(y_i)) + (1 - y_i) \cdot \log(1 - p(y_i))$$

Where:

q—set,

N—number of samples in the set, $y_i$—label for a given sequence (0 or 1), $p(y_i)$—prediction for a given sequence (continuous value between 0 and 1).

Minimizing the mentioned cost function derived from information theory, which is the entropy of the random variable yi (with a slight modification), can be interpreted as the desire to obtain a situation in which the output values will be exactly zero or one for the appropriate classes of signals. Then the function will assume a global minimum equal to zero. However, in practice we get the value of a random variable in the continuous range from 0 to 1, the density of which has higher values near zero and one.

Evaluation of Inventively Trained Deep Learning Neural Network Model:

For evaluation purposes input data accumulated on three different inventive apparatus are used to estimate whether and if yes, how much, the performance of the deep learning neural network is dependent on the differently acquired input data.

Data records were taken on two generations of the inventive apparatus for incubating the respective sample microorganism and taking respective images of the incubated samples over the whole incubation time period.

The inventive apparatus refers to two different generations of BacterOMIC machine. Machine from beta generation is called Beta in the context of the present invention, and the two machines from A generation are called A2 and A3 in the context of the present invention. The main difference between the two generations of the inventive apparatus relates to the different arrangement of microfluidic chip (flipped chip) inside the machine and, thus, in particular different lighting conditions.

The input data is in the form of a sequence of k consecutive (or evenly distributed) images from a specific proportional time period in relation to the full incubation time period covering the standard full incubation time period of the microorganism, wherein k represents a sequence of 2 or more, 8 or more, 16 or more or 24 images, presently a sequence of 16 (mini) images.

Preferably, all pixel intensities of all images may be divided by 255 so that the input to the model is normalized to a range of 0 to 1, which reduces the computational load.

With respect to signal classification in the training phase the inventively used model is fed with evenly extracted sequence of k images with almost equal time steps with respect to the images taken for different samples. In order to cover the whole time dimension of the incubation experiment (full analysing time), the whole incubation time period is completely covered with the input data in the training phase.

With respect to signal prediction in validation or test phase, the progress values $t_p$ may be chosen at 0.2, 0.3, 0.4, 0.5, 0.75 and 0.9 of the experiment length (analyzing time period). This means that the two or more, preferably 16 or more images are (evenly) consecutively distributed within the proportional analyzing time, wherein at the starting point no image is taken and the last image of the k selected images of the sequence is the one taken before 0.2, 0.3, 0.4, 0.5, 0.75 and 0.9 of the run length (analyzing time period) respectively.

Due to the fact that the inventive model is meant to be trained in supervised manner it is fed with binary labels 1 (microorganism growth) or 0 (microorganism growth inhibition) that were obtained by other techniques previously.

Training, validation and test sets have been prepared in such a way that they consist of approximately 50% positive samples relating to microorganism growth (label 1) and approximately 50% negative samples relating to microorganism inhibition (label 0). Due to the equal weights resulting from the equal number of types of samples, it is convenient to use effectivity score as a single evaluation metric. Effectivity is the product of sensitivity and specificity as follows $$\text{effectivity} = \text{sensitivity} \times \text{specificity, wherein}$$

$$\text{sensitivity is represented by}$$

$$\frac{\text{number of true positives } (TP)}{\text{number of true positives } (TP) + \text{number of false negatives } (FN)}$$

$$\text{and}$$

$$\text{specificity is represented by}$$

$$\frac{\text{number of true negatives } (TN)}{\text{number of true negatives } (TN) + \text{number of false positives } (FP)}.$$

The effectivity value cannot be greater than the lower of the sensitivity and specificity value. For this reason, an increase in effectivity means an increase of a weaker parameter, and high values of effectivity mean high values of both sensitivity and specificity and equal balance of the method (no bias for positive or negative classification).

The inventively used model was trained on the largest dataset of records produced by Beta machine and was evaluated on more than 12 thousands of records, i.e. signals from single chamber. To reasonably cover many combinations of microorganism-antibiotic pairs, preferably bacteria-antibiotic pairs test set consisted of runs between 12905 and 12925. They were in Universal panel configuration with more than 40 antibiotics.

The microorganisms used to train the model of the Beta machine relate to bacteria strains, preferably *E. coli* ATCC 25922 and *S. aureus* ATCC 29213, run 12925 was a negative control one (no bacteria used). After obtaining suitable performance on Beta machine the inventors were able to reuse trained model with less or even no training for input data from A2 and A3 machines.

Data aggregated in A2 and A3 machines was a series of tests that were carried out on more than 300 of bacteria strains delivered by Centrum Zdrowia Dziecka (Children's Memorial Health Institute), Warsaw within a preclinical examination phase of BacterOMIC machine. It must be noted that A2 and A3 test datasets were labelled by using the MIC results delivered by a reference method delivered by Centrum Zdrowia Dziecka.

As a next stage, the inventors prepared a training dataset for A2 machine, which is smaller by one order of magnitude, to fine-tune the inventive model.

Analysis of Input Data Acquired from Beta Machine:

For the analysis the inventors used most of the data recorded between 12 Jul. 2019 and 24 Oct. 2019 on Beta machine, a total of 322 experiments, which were divided into training, validation and test sets.

The ratio of positive to negative recorded signals was 1.05:0.95, which was taken into account in the training of the model by assigning an appropriate weight to a given signal class.

The following table 1 is showing the binary classification metrics for input data sets recorded on Beta machine:

TABLE 1

| Binary classification metrics for input data sets recorded on Beta machine | | | | |
|---|---|---|---|---|
| Set | Accuracy | Sensitivity | Specificity | AUC |
| Test | 97.93% | 98.78% | 94.34% | 97.91% |
| Train | 96.94% | 95.37% | 95.78% | 96.94% |
| Val | 96.82% | 95.10% | 95.69% | 96.79% |

In the context of the present invention, the expression "accuracy" refers to the accuracy of a single incubation chamber/compartment of the incubation device/incubation carrier. Such as a microchamber of a microtiter plate.

Analysis of Input Data Acquired from A2 Machine:

The inventors performed 5 epochs of retraining on data recorded by A2 machine with model previously fitted on Beta records. Model converged surprisingly quickly mainly because it should only adjust to mean pixel intensity ($p_i$) of images in A2 machine and also because of only about 12 experiments in training set (about 8 k records). According to the present invention, the property of pixel intensity ($p_i$) per pixel of images is the essential feature to properly predict the classification of the images, as it varies considerably between machines. All other properties of images or sequences of images are mostly the same or highly similar.

Analysis of Input Data Acquired from A3 Machine:

Due to the fact that majority of the performed experiments were to a certain degree flawed in terms of images taken during the analysis we present metrics only for the runs that were examined by expert manually.

Without any fine tuning on the data produced on A3 machine, the inventive prediction method previously fitted on Beta dataset and fine-tuned on A2 machine achieved following overall accuracies of target and range values according to table 2:

TABLE 2

| Overall accuracies of target and range values for test set produced on A3 machine | |
|---|---|
| Target | Range |
| 91% | 97.5% |

Summary

The above example section proves that the inventive method in particular using the inventively trained deep learning neural architecture meets the assumed requirements for predicting microorganism growth or microorganism growth inhibition.

Moreover, the inventive method is extremely easy to fine-tune and is less prone to classify never-seen bright anomalies as positive signals.

In addition, the inventive method and apparatus uses the information on the pixel intensity ($p_i$) of the images for all sequences of images covering the whole incubation time for signal classification purposes. This information, however, is reduced in its dimensionality only for signal prediction using the deep learning neural network. Accordingly, the inventive method is advantageous in comparison to previously proposed methods that were based on parameters chosen by an expert, such as structure/shape of colonies of incubated microorganisms.

Training of the Deep Learning Neural Network with a Separate Models Approach:

This approach is based on the notion that separate models trained on different sub-sequences of the whole images sequences may act better for particular time periods of the analysis. Main argument for this reasoning is that by increasing number of models the computational capacity of the whole system (that is a set of models) is directly increased. Therefore, the system is likely to distinguish more possible bacterial growth behaviours that are related directly to the specific time during the analysis.

For the reason that the system in this approach consists of a set of models training procedure is straight forward. We train one model architecture starting with progress value $t_p=1$ gradually decreasing it. The progress variable stands for a part of the whole sequence of images from the analysis that is fed to the model. In order to have a system which is a collection of models we save every best model (in terms of validation accuracy) from the training for a particular value of progress. For a method validation purposes we were training models with progress value $t_p \in \{0.2, 0.4, 0.6, 0.8, 1\}$.

In the inference stage i.e. during machine opera on only one from the set of models is making predictions for specific time of the analysis.

Training of the Deep Learning Neural Network with a One Model Approach:

As already mentioned, this approach proves to be much more universal and less error prone due to the fact that only one model is trained. However, it is also presumably less capable to learn all the different behaviours of bacteria growths due to much more restricted parameters space in comparison to the collection of the models from previous approach. To the model from this one model approach the inventors additionally fed the mentioned scalar progress value $t_p$ in order to enable the model to autonomously calibrate sensitivity of analysis for a particular time frame.

Training in one model approach runs in different manner, because only one model is trained during the whole training process. In every epoch the progress variable is randomly chosen for every record from the dataset. Randomly choosing the progress variable was conducted in two variances:

- from set {0.2, 0.4, 0.6, 0.8, 1.0}
- from continuous uniform distribution from 0.2 to 1.0 inclusively.

Therefore, in every epoch the inventors received completely different combination of sub-sequences from the original records which serves as data augmentation and leads to better generalization by the model. As already mentioned in this one model approach, the progress variable is also fed to the model as a second input and concatenated with distilled representation from the image sequence. Alternatively, the inventors used this one model approach also without feeding progress to the model.

The inference for the one model is straight forward because only one model is used in this approach. Therefore, for prediction only sequence of images and progress variable is needed in any moment of the analysis.

Figure 10A:
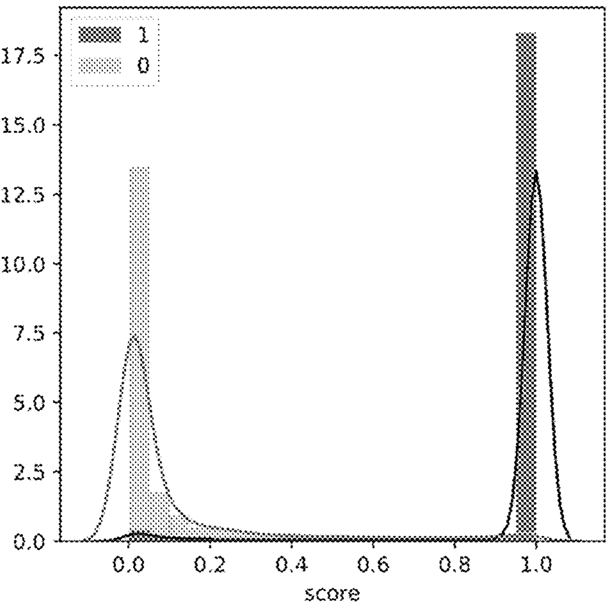
FIGS. 10*a*), 10*b*) represent a histogram of prediction of microorganism growth 1 or microorganism inhibition (0) for a respective test set at progress value 0.6 (FIG. 10*a*)) and a respective confusion matrix (FIG. 10*b*).
Figure 10B:
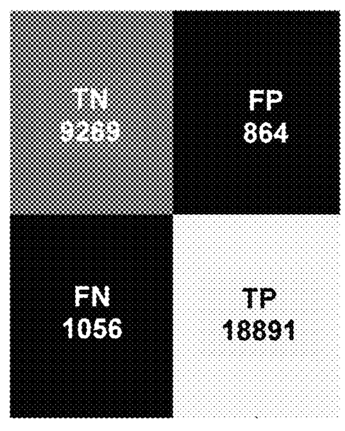
Figure 11A:
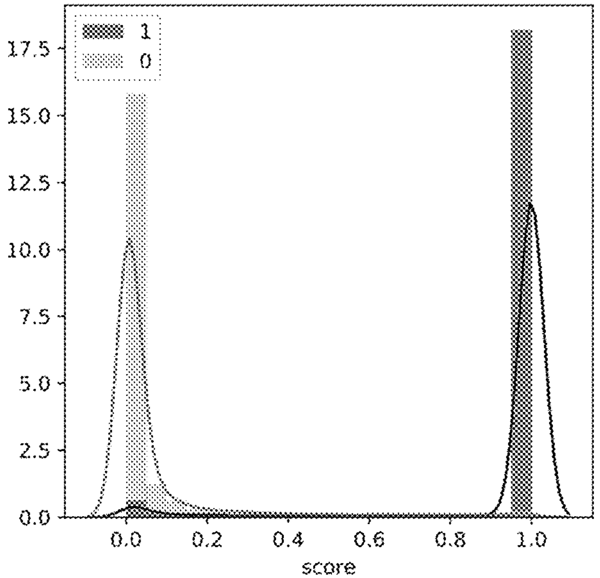
FIGS. 11*a*), 11*b*) represent a histogram of prediction of microorganism growth 1 or microorganism inhibition (0) for a respective test set at progress value 0.8 (FIG. 11*a*)) and a respective confusion matrix (FIG. 11*b*)).
Figure 11B:
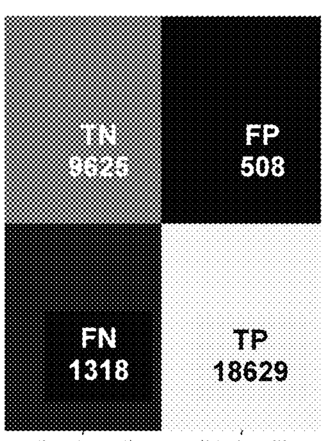
Figure 12A:
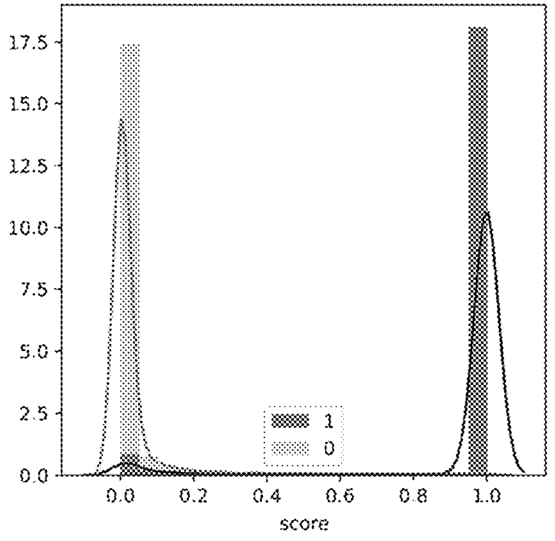
FIGS. 12*a*), 12*b*) represent a histogram of prediction of microorganism growth 1 or microorganism inhibition (0) for a respective test set at progress value 1.0 (FIG. 12*a*)) and a respective confusion matrix (FIG. 12*b*)).
Figure 12B:
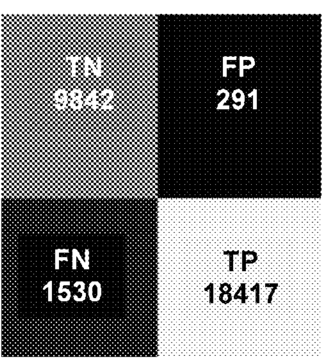

Visualization of Change of Model Prediction in View of Different Progress Values:

To visualize how model predictions are changing in view of different progress values (different continuing incubation), histograms of predictions are presented for 5 different for five different progress values, namely $t_p=0.2$ (see FIGS. 8*a*) and 8*b*), $t_p=0.4$ (see FIGS. 9*a*) and 9*b*), $t_p=0.6$ (see FIGS. 10*a*) and 10*b*), $t_p=0.8$ (see FIGS. 11*a*) and 11*b*), and $t_p=1.0$ (see FIGS. 12*a*) and 12*b*)), i.e. five different analyzing time periods. FIGS. 8*a*), 9*a*), 10*a*), 11*a*) and 12*a*) represent respective histograms of prediction microorganism growth or microorganism growth inhibition and FIGS. 8*b*), 9*b*), 10*b*), 11*b*) and 12*b*) represent respective confusion matrices obtained using threshold for the output score at $S_o$ at 0.5 value of prediction, with number of True Positive (TP), True Negative (TN), False Positive (FP), and False Negative (FN) predictions for the five different progress values of the same dataset.

As can be seen from FIGS. 8 to 12, with increase of progress values, i.e. increase of analyzing time period, the distribution of predicted values are getting denser around 0 and 1, because the model is more confident when predicting sequences that cover broader analyzing time period. It is due to the fact that information density gets higher as time progresses and bacteria starts growing. Consequently, overlap in predicted value distributions between positive and negative classes is diminishing.

Summary on Differences Regarding Separate Model Approach and One Model Approach:

Taking into account results presented above, convenience in inference stage and overall robustness of the solution the one model approach may be chosen.

The obvious observation is that for higher values of progress variable a much better classification metrics may be obtained due to visible growth of bacteria in latter phases of analysis. However, it is worth mentioning that even for sub-sequences from time frames of progress value with max length $t_p$=0.2, the inventive method and system provided reasonable results. Moreover, distribution of predictions shows that the one model approach is highly sensitive and can distinguish even slight increasing trend in the pixel intensity ($p_i$) in the sequence of images from the beginning of the run.

There is also a clear evidence that at the lower values of progress variable model does not favour any of the labels. However, for higher values model distinctively makes more False Negative errors than False Positives which may be due to very low overall pixel intensity ($p_i$) in Beta machine.

Evaluation of Results Retrieved from the Inventive One Model Approach Using Additional Information on Microorganism and Antibiotic:

In addition to above mentioned experiments, the inventors performed experiments in order to show that the additional use of information on the bacteria and/or, in particular and the antibiotics during the training of a one-model approach may have a beneficial influence on the performance (accuracy, sensitivity and/or specificity) of the test results.

Model Used:

In this respect, an inventive one-model approach was used, wherein the layers of the deep learning model sequentially comprise a recurrent layer, preferably ConvLSTM2D layer, to extract spatio-temporal features, a BatchNormalization layer for better generalization effect, a MaxPooling layer, preferably a MaxPooling 3D layer, to further extract spatio-temporal features. This layer arrangement/architecture is followed by second layer architecture comprising a recurrent layer, preferably ConvLSTM2D layer, to extract spatio-temporal features, a BatchNormalization layer for better generalization effect, a MaxPooling layer, preferably a MaxPooling 3D layer, to further extract spatio-temporal features. In other words, a combination of two times a recurrent, preferably a ConvLSTM2D and subsequent MaxPooling layer architecture may provide a suitable prediction of microorganism growth and microorganism growth inhibition of a sequence of images taken with respect to a sample microorganism.

Following the feature extraction, the layer architecture comprises a Flatten layer followed by a Dense layer in order to transform signal for convenient classification. A BatchNormalization and Dropout layer follows for improved regularization and improved generalization. A further Dense layer is subsequently arranged, followed by a BatchNormalization and Dense layer architecture in this order. The resulting fully connected layer represents a Dense layer, preferably with sigmoid activation.

Such a deep learning model is generally described with respect to FIG. 3*f*) in the general description of the present application.

Input Data:

As set out above, the input data is in the form of a sequence of k consecutive (or evenly distributed) images from a specific proportional time period in relation to the full incubation time period covering the standard full incubation time period of the microorganism, wherein k represents a sequence of 2, 3, 4, 5, 6, 7, 8, 9, 10, 11, 12, 13, 14, 15, 16, 17, 18, 19, 20, 21, 22, 23, 24 or more, images, presently k represents a sequence of 16 (mini) images.

The present experiment differed from the above experiments in that in addition information on the following bacteria and antibiotics used during the experiments was also used for the training of the inventive model:

Bacteria (5): *Acinetobacter, Enterobacterales, Enterococcus, Pseudomonas, Staphylococcus;*

Antibiotics (61): Amikacin, Amoxicillin, Amoxicillin-clavulanic acid, Ampicillin, Ampicillin-sulbactam, Azithromycin, Aztreonam, Benzylpenicillin, Cefalexin, Cefazolin, Cefepime, Cefepime-clavulanic acid, Cefixime, Cefotaxime, Cefotaxime-clavulanic, Cefoxitin, Ceftaroline, Ceftazidime, Ceftazidime-avibactam, Ceftazidime-clavulanic acid, Ceftolozane-tazobactam, Ceftriaxone, Cefuroxime iv, Chloramphenicol, Ciprofloxacin, Clarithromycin, Clindamycin, Colistin, Daptomycin, Doxycycline, Ertapenem, Erythromycin, Fosfomycin, Fusidic acid, Gentamicin, Imipenem, Levofloxacin, Linezolid, Mecillinam, Meropenem, Meropenem-EDTA, Meropenem-cloxacillin, Meropenem-phenylboronic acid, Minocycline, Moxifloxacin, Nitrofurantoin, Norfloxacin, Ofloxacin, Oxacillin, Piperacillin, Piperacillin-tazobactam, Rifampicin, Tedizolid, Teicoplanin, Tetracycline, Ticarcillin-clavulanic acid, Tigecycline, Tobramycin, Trimethoprim, Trimethoprim-sulfamethoxazole, Vancomycin.

Input data were retrieved from in-house experiments as Bacteromic Ltd. In Warsaw, Poland, as well as during a clinical trial (data collection April to September 2021) at University of Lodz in Lodz, Nicolaus Copernicus University in Toru, University of Warmia and Mazury in Olsztyn (all locations in Poland).

The input data used for obtaining present results were divided into the following subsets:

Training set: 59 465 samples (chambers), collected in our lab (Bacteromic Ltd.), Validation set: 15 900 samples (chambers), collected in our lab (Bacteromic Ltd.), Test set: 26 477 samples (chambers), collected during the clinical trial in locations other than Bacteromic.

Results:

The results of classification of growth/no-growth in the Training, Validation and Test sets retrieved in this experiment are displayed in the following Table 3:

TABLE 3

| Results on Accuracy, Sensitivity and Specificity of Training, Validation and Test Sets | | | |
|---|---|---|---|
| Set | Accuracy | Sensitivity | Specificity |
| Training | 99.46% | 99.63% | 99.3% |
| Validation | 99.41% | 99.47% | 99.36% |
| Test | 97.7% | 97.89% | 97.32% |

According to the present invention, also the minimum inhibitory concentration (MIC) can be determined in case information on the growth/no-growth behaviour in respective subsequent wells dependent on the antibiotic is used.

The determined MIC reference values obtained by the reference method were compared to real (known) values for each microbial-antimicrobial pair. Overall results of MIC comparison for the present data (1664 MIC tests in the validation set and 2948 MIC tests in the test set) are displayed in the following table 4:

TABLE 4

| Overall Target and Range values for Training, Validation and Test Sets using additional information on antibiotic and bacteria in the inventive test | | |
|---|---|---|
| Set | Target | Range |
| Training | 95.94% | 97.29% |
| Validation | 95.37% | 95.73% |
| Test | 88.70% | 94.44% |

It appears that in comparison to the results not using addition information on antibiotic and bacteria and displayed in Table 2 for Target (91%) and Range (97.5%), the target results using the additional information on the antimicrobial and bacteria for the Test Set (88.70%) and the Range results for the Test and Validation Results (95.37%)

may be lower. However, the results in Table 4 of inventive model using the additional information cover 305 combinations (5 bacteria families and 61 antimicrobial agents), whereas the results in Table 2 instead only cover approximately 80 combinations due to the use of only 2 bacteria families and 40 antibiotic agent types. Thus, no direct comparison of the results in Tables 2 and 4 can be performed.

Instead, in particular improvements on the performance including accuracy, sensitivity and specificity of the inventive method including the additional information on antibiotic agent and bacteria is shown in the following Table 5:

TABLE 5

| Improvements in performance for specific microbial-antimicrobial pairs: | | | | | | | | |
|---|---|---|---|---|---|---|---|---|
| All•numbers•are•%¤ | | Without•additional•information•on•bacteria•and•antibiotic•type¤ | | | With•additional•information•on•bacteria•and•antibiotic•type,•i.e.,•with•$M_v$¤ | | | ¤ |
| Antibiotic¤ | Bacteria¤ | Accuracy¤ | Sensitivity¤ | Specificity¤ | Accuracy¤ | Sensitivity¤ | Specificity¤ | ¤ |
| Minocycline¤ | *Acinetobacter*¤ | 80¤ | 100¤ | 74.71¤ | 100¤ | 100¤ | 100¤ | ¤ |
| Piperacillin-tazobactam¤ | *Acinetobacter*¤ | 81.48¤ | 70¤ | 90¤ | 96.3¤ | 88.24¤ | 100¤ | ¤ |
| Meropenem¤ | *Acinetobacter*¤ | 86.61¤ | 98.33¤ | 98.33¤ | 99.11¤ | 73.08¤ | 100¤ | ¤ |
| Cefalexin¤ | *Enterobacterales*¤ | 89.22¤ | 100¤ | 82.54¤ | 100¤ | 100¤ | 100¤ | ¤ |
| Imipenem¤ | *Enterobacterales*¤ | 90.48¤ | 100¤ | 90.2¤ | 100¤ | 100¤ | 100¤ | ¤ |
| Nitrofurantoin¤ | *Enterobacterales*¤ | 90.48¤ | 100¤ | 85.92¤ | 99.05¤ | 100¤ | 98.59¤ | ¤ |
| Trimethoprim-sulfamethoxazole¤ | *Staphylococcus*¤ | 88.89¤ | 100¤ | 100¤ | 100¤ | 100¤ | 100¤ | ¤ |
| Ceftazidime¤ | *Staphylococcus*¤ | 91.67¤ | 94.29¤ | 86.84¤ | 95.37¤ | 92.86¤ | 100¤ | ¤ |
| Imipenem¤ | *Pseudomonas*¤ | 92.38¤ | 100¤ | 82.22¤ | 100¤ | 100¤ | 100¤ | ¤ |
| Cefepimene¤ | *Pseudomonas*¤ | 91.96¤ | 100¤ | 83.33¤ | 99.11¤ | 100¤ | 98.15¤ | ¤ |
| Vancomycin¤ | *Enterococcus*¤ | 98.15¤ | 97.83¤ | 98.39¤ | 100¤ | 100¤ | 100¤ | ¤ |

REFERENCE NUMERALS

- 10 deep learning neural network configured to extract spatio-temporal features of a sequence of images
- 101 first feature extractor of the deep learning neural network, preferably with one or more recurrent layers, such as ConvLSTM2D layers
- 102 second feature extractor of the deep learning neural network, preferably comprising one or more Dense layers
- 103 classification unit for classifying the respective sequence of images
- b sequence of pixel intensity per pixel for the sequence of two or more images of the incubated sample microorganism
- Δb determined sequence of differences in the pixel intensity ($\Delta p_i$) per pixel between two consecutive images respectively for the sequence of two or more images
- $t_p$ progress value
- k consecutive images, preferably two or more, five or more, eight or more, 16 or more, or 24 images forming a respective sequence of images for the respective progress value $t_p$

The invention claimed is:

1. A computer-implemented method for real-time prediction of microorganism growth or microorganism growth inhibition of a microorganism inoculum in a phenotypic antimicrobial susceptibility test (AST), the method comprising the following steps:

a) Incubating a sample of a microorganism with a suitable incubating device, wherein the incubated sample comprises a single antimicrobial agent or a combination of antimicrobial agents, b) Taking a sequence of two or more digital images of the incubated sample microorganism of step a) with a suitable imaging device and providing information on pixel intensity ($p_i$) per pixel of the two or more digital images, wherein the sequence of the two or more digital images is consecutively distributed within a progress value ($t_p$) with $0<t_p<1$, wherein the progress value $t_p$ represents a ratio of a proportional incubation time period for the consecutively distributed sequence of the two or more digital images of the incubated sample microorganism divided by an overall incubation time period from start to end of the incubation for the respective microorganism, and c) Predicting microorganism growth or microorganism growth inhibition for the incubated sample microorganism as a function of an output score ($S_o$) $0\leq S_o\leq 1$ of a deep learning neural network configured to extract spatio-temporal features of the sequence of the two or more digital images and to classify the respective images, wherein $S_o=0$ represents a distinct microorganism growth inhibition and $S_o=1$ represents a distinct microorganism growth, and wherein the deep learning neural network uses as input data:

(i) a sequence of pixel intensity ($p_i$) per pixel for the two or more digital images of the incubated sample microorganism of step b), or (ii) a determined sequence of differences in the pixel intensity ($\Delta p_i$) per pixel between two consecutive images respectively for the two or more digital images of step b), or (iii) a sequence of pixel intensity ($p_i$) per pixel for the two or more digital images of the incubated sample microorganism of step b) and a determined sequence of differences in the pixel intensity ($\Delta p_i$) per pixel between two consecutive images respectively for the two or more digital images of step b).

2. The computer-implemented method for real-time prediction of microorganism growth or microorganism growth inhibition according to claim 1, wherein the deep neural network further uses as input data:

(iv) a respective progress value $t_p$ used in (i), (ii) or (iii), wherein in (iii) the same progress value $t_p$ and/or (v) information on the antimicrobial agent present in the incubated sample in step a) and/or (vi) information on the microorganism present in the incubated sample in step a).

3. The computer-implemented method for real-time prediction of microorganism growth or microorganism growth inhibition according to claim 2, wherein the progress value is in a range of $0.2\leq t_p\leq 0.9$.

4. The computer-implemented method for real-time prediction of microorganism growth or microorganism growth inhibition according to claim 2, wherein a threshold value $S_T$ of the output score $S_o$ is predetermined as a function of the selected progress value $t_p$, wherein in case the output score $S_o$ exceeds the predetermined threshold value $S_T$ for the selected progress value $t_p$, the sample is classified 1 representing a distinct probability of microorganism growth, or wherein in case the output score $S_o$ is below a predetermined threshold value $S_T$ for the selected progress value $t_p$, the sample is classified 0 representing a distinct probability of microorganism growth inhibition.

5. The computer-implemented method for real-time prediction of microorganism growth or microorganism growth inhibition according to claim 2, wherein the imaging device in step b) is a digital camera.

6. The computer-implemented method for real-time prediction of microorganism growth or microorganism growth inhibition according to claim 2, wherein the deep learning neural network of step c) comprises one or more recurrent layers.

7. The computer-implemented method for real-time prediction of microorganism growth or microorganism growth inhibition according to claim 1, wherein the progress value is selected from the range $0.2\leq t_p\leq 0.9$.

8. The computer-implemented method for real-time prediction of microorganism growth or microorganism growth inhibition according to claim 1, wherein a threshold value $S_T$ of the output score $S_o$ is predetermined as a function of the selected progress value $t_p$, wherein in case the output score $S_o$ exceeds the predetermined threshold value $S_T$ for the selected progress value $t_p$, the sample is classified 1 representing a distinct probability of microorganism growth, or wherein in case the output score $S_o$ is below a predetermined threshold value $S_T$ for the selected progress value $t_p$, the sample is classified 0 representing a distinct probability of microorganism growth inhibition.

9. The computer-implemented method for real-time prediction of microorganism growth or microorganism growth inhibition according to claim 1, wherein the imaging device in step b) is a digital camera.

10. The computer-implemented method for real-time prediction of microorganism growth or microorganism growth inhibition according to claim 1, wherein the deep learning neural network of step c) comprises one or more recurrent layers.

11. The computer-implemented method for real-time prediction of microorganism growth or microorganism growth inhibition according to claim 1, wherein the deep learning neural network of step c) is free of recurrent layers and comprises one or more convolutional layers, BatchNormalizing layers and ReLU activation layers in order to extract spatio-temporal features of the images.

12. The computer-implemented method for real-time prediction of microorganism growth or microorganism growth inhibition according to claim 1, wherein a spatio-temporal feature extraction of the deep learning neural network in step c) is followed by feature transformation using one or more Dense layers.

13. The computer-implemented method for real-time prediction of microorganism growth or microorganism growth inhibition according to claim 1, wherein the deep learning neural network used in step c) was previously trained:

with a separate models approach comprising two or more models, wherein each model is respectively trained with sequences of two or more digital images of a sample of incubated microorganism for a respective progress value selected from the range $0\leq t_p\leq 1$ as input data, wherein the two or more digital images respectively provide information on the pixel intensity ($p_i$) per pixel and are respectively binary labelled with 0 representing microorganism growth or 1 representing microorganism growth inhibition and wherein the two or more digital images are consecutively distributed within the respective progress value $t_p$, or with a one model approach, wherein in each training epoch the same model is trained with a respective sequence of two or more digital images of a sample of incubated microorganism as input data, wherein the images respectively provide information on the pixel intensity ($p_i$) per pixel and are respectively binary labelled with 0 representing microorganism growth or 1 representing microorganism growth inhibition and wherein the images are consecutively distributed for a respective randomly selected progress value $t_p$, wherein the random selection of the progress value $t_p$ is conducted from a set of {0.2, 0.3, 0.4, 0.5, 0.6, 0.75, 0.8, 0.9, 1.0} or from a continuous distribution in the range of $0.2 \leq t_p \leq 1.0$.

14. The computer-implemented method for real-time prediction of microorganism growth or microorganism growth inhibition according to claim 13, wherein the separate models approach or the one model approach is respectively optimized with respect to the density of the output score $S_o$ for the binary values 0 And 1.

15. The computer-implemented method for real-time prediction of microorganism growth or microorganism growth inhibition according to claim 1, wherein the microorganism is selected from the group consisting of bacterium, *mycobacterium* and fungus.

16. The computer-implemented method for real-time prediction of microorganism growth or microorganism growth inhibition according to claim 1, wherein in step a) two or more samples of the same or of different microorganisms are separately incubated with the incubating device, and wherein in step b) each image of the sequence of the two or more digital images respectively comprises images of the separately incubated two or more sample microorganisms of step a) and wherein each digital image is respectively transformed to form a matrix providing separate images for the respective two or more sample microorganisms as respective input data for the deep learning neural network in step c).

17. A rapid antimicrobial susceptibility testing system for predicting microorganism growth or microorganism growth inhibition of a microorganism inoculum in a phenotypic antimicrobial susceptibility test (AST), the system comprising:

a) an incubation assembly configured for housing an incubation device for incubating a sample of a microorganism, wherein the sample comprises a single antimicrobial agent or a combination of antimicrobial agents, b) an imaging device configured to taking a sequence of two or more digital images of the incubated sample microorganism of feature a) on the incubating device, wherein the imaging device is configured to provide information on pixel intensity (pi) per pixel for each of the two or more digital images and wherein the imaging device is further configured to taking the sequence of the two or more digital images consecutively distributed within a progress value ($t_p$) with $0<t_p<1$, wherein the progress value $t_p$ represents a ratio of a proportional incubation time period for the consecutively distributed sequence of the two or more digital images of the incubated sample microorganism divided by an overall incubation time period from start to end of the incubation for the respective microorganism, and c) a computer assembly comprising one or more processors, and an analysis module comprising a deep neural network unit configured to extract spatio-temporal features of the sequence of the two or more digital images and to classify the two or more digital images and one or more computer-readable media storing instructions that, when executed by the one or more processors, cause the one or more processors to perform predicting microorganism growth or microorganism growth inhibition for the incubated sample microorganism as a function of an output score ($S_o$) $0 \leq S_o \leq 1$ of the deep learning neural network, wherein $S_o=0$ represents a distinct microorganism growth inhibition and $S_o=1$ represents a distinct microorganism growth, and wherein the deep learning neural network is configured to use as input data:

(i) a sequence of pixel intensity ($p_i$) per pixel for the two or more images of the incubated sample microorganism of feature b), or (ii) a determined sequence of differences in the pixel intensity ($\Delta p_i$) per pixel between two consecutive images respectively for the two or more images of feature b), or (iii) a sequence of pixel intensity ($p_i$) per pixel for the two or more images of the incubated sample microorganism of feature b) and a determined sequence of differences in the pixel intensity ($\Delta p_i$) per pixel between two consecutive images respectively for the two or more images of feature b).

18. The rapid antimicrobial susceptibility testing system for predicting a probability of microorganism growth or microorganism growth inhibition according to claim 17, wherein the deep neural network further uses as input data:

(iv) a respective progress value $t_p$ used in (i), (ii) or (iii), wherein in (iii) the same progress value $t_p$ is used, and/or (v) information on the antimicrobial agent present in the incubated sample in step a) and/or (vi) information on the microorganism present in the incubated sample in step a).

19. The rapid antimicrobial susceptibility testing system for predicting a probability of microorganism growth or microorganism growth inhibition according to claim 17, wherein the incubation assembly is configured for housing one or more incubation devices.

* * * * *